United States Patent
Kato et al.

(10) Patent No.: US 11,572,578 B2
(45) Date of Patent: Feb. 7, 2023

(54) REAGENT KIT FOR DETECTING BIOFILM AND METHOD FOR DETECTING BIOFILM

(71) Applicant: SARAYA CO., LTD., Osaka (JP)

(72) Inventors: Yoriko Kato, Kashiwara (JP); Yuka Oda, Kashiwara (JP); Emiko Kawamukai, Kashiwara (JP); Yoshihiko Hirata, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 0 days.

(21) Appl. No.: 17/263,851

(22) PCT Filed: Jul. 31, 2019

(86) PCT No.: PCT/JP2019/029993
§ 371 (c)(1),
(2) Date: Jan. 27, 2021

(87) PCT Pub. No.: WO2020/027192
PCT Pub. Date: Feb. 6, 2020

(65) Prior Publication Data
US 2021/0262002 A1   Aug. 26, 2021

(30) Foreign Application Priority Data

Jul. 31, 2018 (JP) .............................. JP2018-144610
Aug. 23, 2018 (JP) .............................. JP2018-155979
Nov. 28, 2018 (JP) .............................. JP2018-222063

(51) Int. Cl.
*C12Q 1/04* (2006.01)

(52) U.S. Cl.
CPC ..................................... *C12Q 1/04* (2013.01)

(58) Field of Classification Search
None
See application file for complete search history.

(56) References Cited

U.S. PATENT DOCUMENTS

| | | | |
|---|---|---|---|
| 5,912,114 A | 6/1999 | Hutchinson et al. | |
| 9,145,574 B2 * | 9/2015 | Schultz | C12Q 1/04 |
| 9,927,438 B2 | 3/2018 | Schultz et al. | |
| 2014/0161728 A1 * | 6/2014 | Bowler | G01N 33/582 |
| | | | 424/9.6 |

FOREIGN PATENT DOCUMENTS

| | | |
|---|---|---|
| EP | 0864864 A1 | 9/1998 |
| EP | 1248106 A1 | 10/2002 |
| JP | H10-206424 A | 8/1998 |
| JP | H10-309280 A | 11/1998 |
| JP | H11-190736 A | 7/1999 |
| JP | 2012-512857 A | 6/2012 |
| JP | 2014-500495 A | 1/2014 |
| JP | 5466782 B1 | 4/2014 |
| JP | 2016-021888 A | 2/2016 |
| WO | WO 2010/070292 A1 | 6/2010 |
| WO | WO 2012/072980 A1 | 6/2012 |

OTHER PUBLICATIONS

Leaper et al., "Extending the TIME concept: what have we learned in the past 10 years?" *Int. Wound J.*, 9(Suppl. 2): 1-19 (2014).
Nakagami et al., "Innovation of Wound Care by Visualizing Biofilms," *Japanese Journal of Foot Care*, 16(1): 1-6 (2018).
Nakagami et al., "Visualizing Biofilms," *Visual Dermatology*, 17(2): 156-159 (2018).
Nakagami, "New wound care utilizing biofilm detection technology that can be performed at the bedside," *JSWH News Letter*, 105 (2018).
Japanese Patent Office, International Search Report in International Patent Application No. PCT/JP2019/029993 (dated Oct. 29, 2019).
European Patent Office, Extended European Search Report in European Patent Application No. 19843360.9 (dated Mar. 31, 2022).

* cited by examiner

*Primary Examiner* — Vera Afremova
(74) *Attorney, Agent, or Firm* — Leydig, Voit & Mayer, Ltd.

(57) ABSTRACT

The present invention relates to a reagent kit for detecting biofilm in test tissue, the reagent kit comprising:
(a) a pretreatment liquid comprising at least one surfactant selected, from the group consisting of nonionic surfactants, amphoteric surfactants, and cationic surfactants,
(b) a staining liquid comprising a dye, and
(c) a decolorizing liquid comprising at least one surfactant selected from the group consisting of nonionic surfactants, amphoteric surfactants, and cationic surfactants;
wherein after a membrane is brought into contact with the test tissue and released from contact, the pretreatment liquid (a), the staining liquid (b), and the decolorizing liquid (c) are brought into contact with the contact surface of the membrane in this order.

15 Claims, 6 Drawing Sheets

(1) Step 2 (pretreatment step)

(2) Step 3 (staining step)

(3) Step 4 (decolorization step)

(1) Step 2 (pretreatment step)

(2) Step 3 (staining step)

(3) Step 4 (decolorization step)

| Type of surfactant used in steps 2 and 4 | | Evaluation results | |
|---|---|---|---|
| | | Immediately after decolorization | After drying |
| Nonionic | (1) Polysorbate 80 | | |
| | (2) Polyoxyethylene lauryl ether | | |
| | (3) Polyoxyalkylene alkyl ether | | |
| Amphoteric | (7) Lauryldimethylaminoacetic acid betaine | | |
| | (8) Lauryldimethylamine oxide | | |
| Anionic | (11) Sodium polyoxyethylene lauryl ether sulfate | | |

FIG. 6

| Bacterial species | Evaluation results | |
|---|---|---|
| | Immediately after decolorization | After drying |
| Pseudomonas aeruginosa PAO-1 | | |
| Pseudomonas aeruginosa ATCC 27853 | | |
| Staphylococcus aureus ATCC 29213 | | |
| Mixture of the three bacteria | | |
| Uncultured pig skin piece | | |

REAGENT KIT FOR DETECTING BIOFILM AND METHOD FOR DETECTING BIOFILM

CROSS-REFERENCE TO RELATED APPLICATIONS

This patent application is the U.S. national phase of International Patent Application No. PCT/JP2019/029993, filed Jul. 31, 2019, which claims the benefit of Japanese Patent Application No. 2018-144610, filed Jul. 31, 2018, Japanese Patent Application No. 2018-155979, filed Aug. 23, 2018, and Japanese Patent Application No. 2018-222063, filed Nov. 28, 2018, which are incorporated by reference in their entireties herein.

TECHNICAL FIELD

The present application claims priority based on Japanese Patent Application No. 2018-144610 filed on Jul. 31, 2018, Japanese Patent Application No. 2018-155979 filed on Aug. 23, 2018, and Japanese Patent. Application No. 2018-222063 filed on Nov. 28, 2018, the entire disclosures of ail of which are incorporated herein by reference. The present invention relates to a method for detecting the presence of biofilm in raw tissue, and a reagent kit for use in the method.

BACKGROUND ART

Chronic wounds, such as pressure ulcers (pressure injuries) and diabetic foot ulcers, have an extremely high risk of developing infections, because they are constantly exposed to external bacteria and the host's immunity is weakened. In recent years, it has become clear that bacterial biofilms are involved in the pathophysiology of chronic wounds. Biofilm-based wound management, which manages wounds depending on the presence of biofilm, has been emphasized.

Biofilm is a community formed by the fixation of microorganisms, and its main constituents are glycoproteins, proteins, extracellular DNA, etc. Biofilm is present as a reservoir of bacteria and expresses pathogenicity by forming a population. Further, biofilm can evade the effects of antibacterial agents and host immunity, causing chronic inflammation and becoming a very strong source of infection (see NPL 1). Therefore, healing cannot be expected as long as biofilm is present at the bottom of the wound. For this reason, since the latter half of the first decade of the 2000s, it has been advocated that, as biofilm-based wound therapy, wound treatment should be selected depending on the presence of biofilm. Specifically, the international guidelines jointly published by the European, US, and Pan Pacific Pressure Ulcer Advisory Panel (EPUAP-NPUAP-PPPIA) in 2014 include the section "Assessment and treatment of infection and biofilms," where the management method is explained. The guidelines recommend suspecting the presence of biofilm when, for example, the wound has been present for more than 4 weeks, there are no signs of healing for the past 2 weeks, there are findings of inflammation, or there is antimicrobial resistance. However, implementation in clinical practice is difficult because a definitive diagnosis of the presence of biofilm requires tissue biopsy and microscopic observation (see NPL 1 above).

Accordingly, there have recently been proposed technologies for quickly visualizing the distribution of biofilm on the wound surface by detecting polysaccharide components, which are constituents of biofilm, by application of wound blotting, which is a method for detecting trace components present on the wound surface (e.g., PTL 1, PTL 2, and NPL 2 to NPL 4).

PTL 1 discloses a method for visualizing the distribution of biofilm on a wound surface by wound blotting using a membrane containing a ligand for detecting trace components (anionic bacterial exopolysaccharides, such as poly-β-(1-6)-N-acetyl-D-glucosamine and alginic acid) present in the extracellular matrix of biofilm. However, this method requires about 30 minutes for detection, and is not suitable for use in clinical practice, particularly at the bedside. In order to improve this, PTL 2 discloses a method for directly detecting biofilm by wound blotting without using a biofilm-specific detection ligand. Specifically, this method comprises bringing a positively charged membrane (e.g., a cationic nylon membrane) into contact with a wound surface, staining the membrane removed from the wound surface with a cationic dye (e.g., ruthenium red or alcian blue), and cleaning the stained membrane with an aqueous solution containing acetic acid and 3 to 2% low alcohol, whereby negatively charged trace components derived from biofilm can be stained in a state of adhering to the membrane. Although this method can shorten the detection time compared with the method of PTL 1, it is not yet sufficient. Further, due to the use of acetic acid, which has a pungent odor, as a component of the membrane cleaning solution, this method is not suitable for implementation at the bedside.

NPL 2 to NPL 4 disclose methods for visualizing biofilm by cleaning a wound surface, then attaching a nitrocellulose membrane to the wound surface for 10 seconds, and then immersing the membrane in a staining liquid (ruthenium red or alcian blue) specific to polysaccharide components derived from biofilm. According to these methods, the time required for detection is about 2 minutes, and biofilm can be detected easily in a short time and non-invasively at the bedside. Therefore, an index for cleaning the wound can be obtained, and more appropriate local management of wounds is possible.

CITATION LIST

Patent Literature

PTL 1: U.S. Pat. No. 9,145,574B2
PTL 2: U.S. Pat. No. 9,927,438B2

Non-Patent Literature

NPL 1: David J Leaper, et al., Extending the TIME concept: What have we learned in the past 10 years? International Wound Journal 2014; 9 (Suppl. 2): pp. 1-19 (pages 6-7 are particularly related)
NPL 2: Gojiro Nakagami et al., "Transformation of wound care with biofilm visualization," Journal of the Japanese Society of Footcare, 2018: 16(1); pp. 1-6
NPL 3: Gojiro Nakagami et al., "Visualize biofilm," Visual Dermatology Vol. 17, No. 2, 2018; pp. 156-159
NPL 4: Gojiro Nakagami, "New wound care utilizing biofilm detection technology that can be performed at the bedside," JSWH News Letter, May 2018; No. 105

SUMMARY OF INVENTION

Technical Problem

An object of the present invention is to provide a method for detecting the presence of biofilm in raw tissue, and a reagent kit for use in the method. More preferably, an object of the present invention is to provide a method for detecting biofilm easily in a short time and non-invasively at the bedside, and a reagent kit for use in the method.

Solution to Problem

As a result of extensive studies to solve the above problems, the present inventors confirmed that as a method for detecting the presence of biofilm in a wound by wound blotting, a membrane attached to the wound was immersed in a pretreatment liquid containing a surfactant other than anionic surfactants, followed by staining treatment and washing treatment (decolorization treatment), whereby the presence of biofilm on the membrane could be clearly visualized in a short time. Further, the present inventors found that according to this method, the visualization of biofilm was stable and became even clearer not only immediately after the decolorization treatment but also after the membrane dried. Therefore, according to the wound blotting of the present invention, the detection of biofilm on the wound surface can be carried out easily and promptly at the bedside and confirmed; in addition, it can be effectively used as an index for subsequent reconfirmation and subsequent removal of biofilm from the wound surface.

The present invention has been completed based on these series of findings, and has the following embodiments.

(I) Biofilm Detection Reagent Kit

I-1

A reagent kit for detecting biofilm in test tissue, the reagent kit comprising:
(a) a pretreatment liquid comprising at least one surfactant selected from the group consisting of nonionic surfactants, amphoteric surfactants, and cationic surfactants,
(b) a staining liquid comprising a dye, and
(c) a decolorizing liquid comprising at least one surfactant selected from the group consisting of nonionic surfactants, amphoteric surfactants, and cationic surfactants;
wherein after a membrane is brought into contact with the test tissue and released from contact, the pretreatment liquid (a), the staining liquid (b), and the decolorizing liquid (c) are brought into contact with the contact surface of the membrane in this order.

I-2

The reagent kit for detecting biofilm according to (I-1), wherein the pretreatment liquid (a), the staining liquid (b), and the decolorizing liquid (c) are each contained in separate containers, preferably containers with a lid that can be opened and closed.

I-3

The reagent kit for detecting biofilm according to (I-1) or (I-2), wherein the surfactant used in the pretreatment liquid (a) and/or the decolorizing liquid (c) is a cationic surfactant selected from dialkyldimethyl ammonium chloride and benzalkonium chloride; an amphoteric surfactant selected from alkyldimethylaminoacetic acid betaine and alkyldimethylamine oxide; or a nonionic surfactant selected from a polyoxyethylene sorbitan fatty acid ester, a polyoxyalkylene alkyl ether, an alkyl polyglucoside, a polyoxyethylene polyoxypropylene glycol, and a polyglycerol fatty acid ester.

I-4

The reagent kit for detecting biofilm according to any one of (I-1) to (I-3), wherein the pretreatment liquid (a) and the decolorizing liquid (c) are aqueous solutions having the same composition.

I-5

The reagent kit for detecting biofilm according to any one of (I-1) to (I-4), further comprising a membrane capable of adsorbing biofilm and/or components thereof present in the test tissue.

I-6

The reagent kit for detecting biofilm according to any one of (I-1) to (I-5), further comprising an instruction manual.

I-7

The reagent kit for detecting biofilm according to any one of (I-1) to (I-6), further comprising at least one auxiliary device selected from an immersion container, a draining member, a waste liquid container, a container with a drainer, tweezers, sterile distilled water, and a dryer.

(II) Biofilm Detection Method

II-1

A method for detecting biofilm in test tissue, comprising the following steps 1 to 4:
(1) step 1 of bringing a membrane capable of adsorbing biofilm and/or components thereof into contact with test tissue;
(2) step 2 of releasing the membrane from contact with the test tissue, and then treating at least the contact surface of the membrane with the test tissue with (a) a pretreatment liquid comprising at least one surfactant selected from the group consisting of nonionic surfactants, amphoteric surfactants, and cationic surfactants;
(3) step 3 of treating, with (b) a staining liquid comprising a dye, at least the contact surface with the test tissue of the membrane treated with the pretreatment liquid (a); and
(4) step 4 of treating, with (c) a decolorizing liquid comprising at least one surfactant selected from the group consisting of nonionic surfactants, amphoteric surfactants, and cationic surfactants, at least the contact surface with the test tissue of the membrane treated with the staining liquid (b).

II-2

The biofilm detection method according to (II-1), wherein the surfactant used in the pretreatment liquid (a) and/or the decolorizing liquid (c) is a cationic surfactant selected from dialkyldimethyl ammonium chloride and benzalkonium chloride; an amphoteric surfactant selected from alkyldimethylaminoacetic acid betaine and alkyldimethylamine oxide; or a nonionic surfactant selected from a polyoxyethylene sorbitan fatty acid ester, a polyoxyalkylene alkyl ether, an alkyl polyglucoside, a polyoxyethylene polyoxypropylene glycol, and a polyglycerol fatty acid ester.

II-3

The biofilm detection method according to (II-1) or (II-2), wherein the pretreatment liquid (a) and the decolorizing liquid (c) are aqueous solutions having the same composition.

II-4

The biofilm detection method according to any one of (II-1) to (II-3), wherein the step (2) of (2) is performed for 2 to 60 seconds, preferably 2 to 30 seconds; the step 3 of (3) is performed for 5 to 60 seconds, preferably 10 to 30 seconds; and the step 4 of (4) is performed for 10 to 120 seconds, preferably 10 to 60 seconds.

II-5

The biofilm detection method according to any one of (II-1) to (II-4), wherein the test tissue is raw tissue in a wound with signs of clinical infection, a refractory wound, or a chronic wound (pressure ulcer, diabetic foot ulcer, or leg ulcer).

II-6

The biofilm detection method according to any one of (II-1) to (II-5), further comprising step 5 of determining whether biofilm is present in the test tissue.

II-7

The biofilm detection method according to (II-6), wherein step 5 is a step of determining that biofilm is present in the test tissue when the contact surface with the test tissue of the membrane treated with the decolorizing liquid has a dye-derived coloring (a contrast image) that contrasts with the background color of the membrane.

II-8

The biofilm detection method according to any one of (II-1) to (II-7), wherein steps 2 to 4 are performed in any of the following ways (i) to (iii):
(i) steps 2 to 4 are performed by sequentially replacing the pretreatment liquid, the staining liquid, and the decolorizing liquid in an immersion container containing the membrane obtained in step 1;
(ii) steps 2 to 4 are performed by sequentially taking the membrane obtained in step 1 in and out of immersion containers separately containing the pretreatment liquid, the staining liquid, and the decolorizing liquid; and
(iii) steps 2 to 4 are performed by placing the membrane obtained in step 1 on the drainer surface of a container with a drainer, and sequentially spraying or dropping the pretreatment liquid, the staining liquid, and the decolorizing liquid so as to spread over the entire surface of the membrane.

Advantageous Effects of Invention

According to the biofilm detection reagent kit of the present invention or the biofilm detection method of the present invention, the presence of biofilm in test tissue, particularly raw tissue, can be detected non-invasively, visually quickly, and clearly. Therefore, according to the present invention, visualization and detection of biofilm can be easily performed in a short time, at the time of medical examination or at the bedside. As a result, wound management is possible in clinical practice, such as promptly removing biofilm on the spot and deciding the treatment policy. In particular, a preferred embodiment of the biofilm detection reagent kit of the present invention includes one having a staining liquid containing alcian blue as a dye component. Since the staining liquid is excellent in long-term storage at room temperature in the form of an aqueous solution, it can be distributed on the market in the state of a pre-prepared solution that does not require preparation at the time of use.

BRIEF DESCRIPTION OF DRAWINGS

FIG. 5 shows, among the results of Verification Experiment 1, the results of implementing the biofilm detection system using aqueous solutions each containing, as the pretreatment liquid and decolorizing liquid, a nonionic surfactant ((1) polysorbate 80, (2) polyoxyethylene lauryl ether, or (3) polyoxyalkylene alkyl ether), an amphoteric surfactant ((7) lauryldimethylaminoacetic acid betaine or (8) lauryldimethylamine oxide), or an anionic surfactant ((11) sodium polyoxyethylene lauryl ether sulfate). The images show the colored state of the membranes immediately after decolorization and after drying. The spots shown in each image correspond to the locations where 2 μL of biofilm suspension was dropped (left side) and 10 μL of biofilm suspension was dropped (right side).

FIG. 6 shows images showing the colored state of blotting membranes after the decolorization treatment (immediately after decolorization and after drying) in the biofilm detection system in which blotting was performed using model wound surfaces (pig skin) in Experimental Example 2.

DESCRIPTION OF EMBODIMENTS

1. Explanation of Terms

Figure 1:
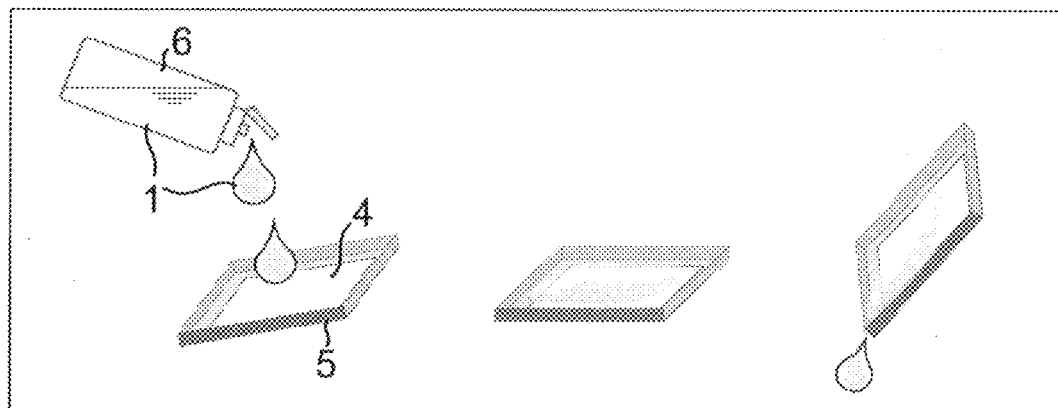
FIG. 1 is a schematic diagram showing an embodiment of (1) step 2 (pretreatment step), (2) step 3 (staining step), and (3) step 4 (decolorization step) in the biofilm detection system of the present invention.
Figure 1:
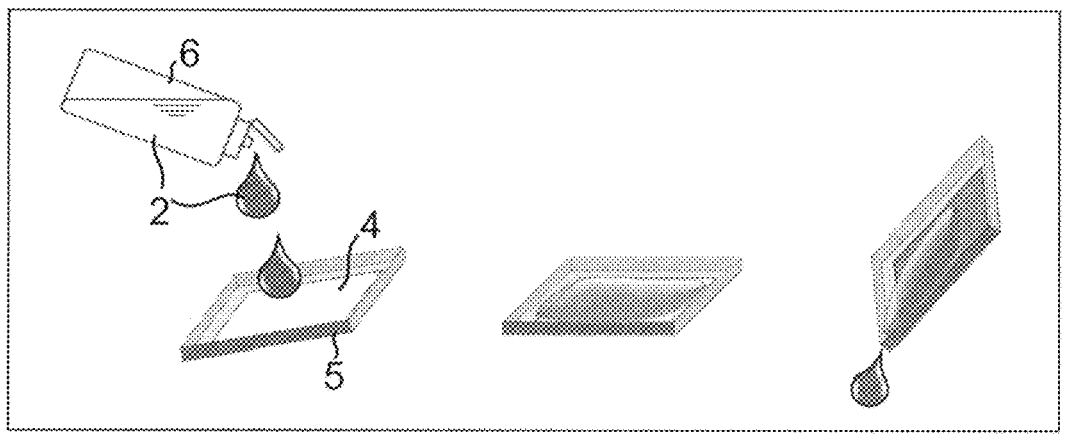
Figure 1:
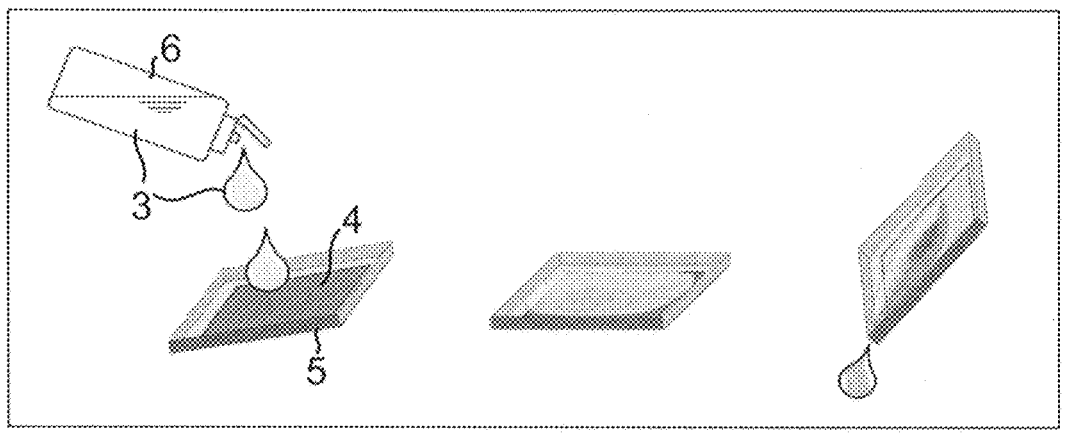

Biofilm is a complex microbial community composed of bacteria encased in an extracellular matrix. The biofilm extracellular matrix contains polyanionic extracellular polysaccharides (e.g., acidic mucopolysaccharides such as poly-β-(1-6)-N-acetyl-D-glucosamine and alginic acid), proteins, extracellular DNA, lipids, and metal, ions (e.g., Ca, Mg, and Fe). The term "biofilm components" as used herein includes biofilm and fragments thereof, as well as, among the components constituting the biofilm extracellular matrix, particularly polyanionic extracellular polysaccharides characteristic of the biofilm extracellular matrix. That is, unless otherwise specified, the term "biofilm components" is used as a general term that includes biofilm and fragments thereof, as well as, among the components constituting the biofilm extracellular matrix, particularly polyanionic extracellular polysaccharides characteristic of the biofilm.

Blotting is a technique for fixing biomolecules to membranes by adsorption. Membranes used for this purpose are called blotting membranes. The wound surface means the surface of a wound, and sometimes includes not only the wound but also the surrounding skin surface. Wound blotting is a technique for non-invasively visualizing the invisible physiological state of the skin, including the wound surface, by blotting mentioned above.

The biofilm detection targeted by the present invention is an application of wound blotting mentioned above. Basically, this technique comprises (A) a step of attaching a blotting membrane to a wound and its surrounding skin (wound surface) that have been pre-cleaned and optionally pretreated (e.g., wiping off water), and collecting biofilm components on the membrane surface (biofilm component collection step), and (B) a step of staining the blotting membrane removed from the wound surface (staining step); and detects the presence of biofilm on the wound surface based on the coloring results of the stained blotting membrane.

2. Biofilm Detection Reagent Kit

The biofilm detection reagent, kit of the present invention (hereinafter, also simply referred to as "the reagent kit") is a reagent kit for use in the detection of biofilm in test tissue. The reagent kit can be preferably used as a reagent for biofilm detection in a biofilm detection system with the application of wound blotting.

Although the biofilm detection system is not limited, an example is a biofilm detection system having the following steps 1 to 5. The details of the biofilm detection system will be described later; however, the pretreatment liquid, staining liquid, and decolorizing liquid contained in the reagent, kit can be used in steps 2, 3, and 4, respectively, among the following steps. All of these steps are for treating the blotting membrane attached to a wound surface to adsorb biofilm components in step 1.

Step 1: Biofilm component collection step
Step 2: Pretreatment step (for blotting membrane)
Step 3: Staining step (for blotting membrane)
Step 4: Decolorization step (for blotting membrane)
Step 5: Biofilm detection and determination step The reagent kit is characterized by comprising at least (a) a pretreatment liquid, (b) a staining liquid, and (c) a decolorizing liquid, described below, each contained in a separate container:

(a) a pretreatment liquid comprising at least one surfactant selected from the group consisting of nonionic surfactants, amphoteric surfactants, and cationic surfactants,
(b) a staining liquid comprising a dye, and
(c) a decolorizing liquid comprising at least one surfactant selected from the group consisting of nonionic surfactants, amphoteric surfactants, and cationic surfactants.

The reagents contained in the reagent kit will be described below in relation to steps 2 to 4 of the biofilm detection system.

(a) Pretreatment Liquid

The pretreatment liquid is a reagent used to treat the blotting membrane obtained in step 1. When biofilm is present on the wound surface, the biofilm and/or components thereof (biofilm components) are adsorbed on the contact surface with the wound surface of the blotting membrane obtained in step 1. The pretreatment liquid is used to treat the blotting membrane in step 2 (pretreatment step) prior to step 3 (staining step). When the treatment with the pretreatment liquid is performed prior to the staining treatment, the part of the blotting membrane on which no biofilm components are adsorbed can be prevented from being stained, and the dye can be prevented from being fixed (coloring); thus, it is possible to prevent a decrease in contrast with the colored portion due to the biofilm components, that is, a decrease in detection sensitivity and accuracy. In other words, the treatment with the pretreatment liquid corresponds to blocking treatment for suppressing non-specific coloring of the membrane with the dye.

The pretreatment liquid is prepared as an aqueous solution comprising at least one surfactant selected from the group consisting of nonionic surfactants, amphoteric surfactants, and cationic surfactants. The nonionic surfactant, amphoteric surfactant, and cationic surfactant are not particularly limited as long as the effect of the present invention can be achieved. Nonionic surfactants are preferable.

Examples of nonionic surfactants include ether surfactants, such as polyoxyethylene (POE) alkyl ether (e.g., POE lauryl ether) obtained by addition polymerization of ethylene oxide (EO) to a $C_{10-18}$ is higher alcohol, polyoxyalkylene alkyl ether, polyoxyethylene (POE) polyoxypropylene glycol (e.g., POE (3) polyoxypropylene glycol (17)) obtained by addition polymerization of EO to polypropylene glycol, and polyoxyethylene alkyl allyl ether (e.g., POE nonylphenyl ether) obtained by addition polymerization of EO to alkylphenol; ether ester surfactants, such as polyoxyethylene sorbitan fatty acid esters (e.g., polysorbates 20, 40, 60, 65, 80, and 85); alkyl polyglycosides comprising sugars (e.g., glucose) as main components; ester surfactants, such as polyglycerol fatty acid esters (e.g., decaglyceryl monocaprate, polyglyceryl monolaurate, and decaglyceryl monomyristate); and the like. Preferred among these are POE lauryl ether, polyoxyalkylene alkyl ether, POE polyoxypropylene glycol, polyoxyethylene sorbitan fatty acid esters, alkyl polyglycosides, and decaglyceryl monocaprate. More preferred are POE lauryl ether, polyoxyalkylene alkyl ether, and polysorbate 80.

Examples of amphoteric surfactants include alkyl betaine surfactants, such as alkyldimethylaminoacetic acid betaine (e.g., lauryldimethylaminoacetic acid betaine); and amine oxide surfactants, such as alkyldimethylamine oxides (e.g., lauryldimethylamine oxide).

Examples of cationic surfactants include dialkyldimethyl ammonium chlorides (e.g., didecyldimethyl ammonium chloride), and quaternary ammonium salt surfactants such as benzalkonium chloride having a $C_{8-18}$ long-chain alkyl group.

These surfactants can be used singly or in any combination of two or more. Nonionic surfactants are preferable because they exhibit stable effects in a relatively wide range of concentrations. Preferred among these are POE lauryl ether, polyoxyalkylene alkyl ether, and polyoxyethylene sorbitan fatty acid esters typified by polysorbate 80.

The pretreatment liquid is preferably used in the form of an aqueous solution in which such a surfactant is dissolved in water. The water used herein is not particularly limited, and examples include tap water, distilled water, ion exchanged water, purified water, sterile water, and the like. The concentration of the surfactant in the pretreatment liquid can be appropriately selected from the range of 0.001 to 20 mass %, as shown in Verification Experiment 1 described later. The lower limit value is, for example, preferably 0.005 mass % or more, and more preferably 0.01 mass % or more. Further, the upper limit value is preferably 10 mass % or less. As shown in Verification Experiment 1, the pH of the pretreatment liquid does not make a significant difference in effectiveness, and the pretreatment liquid can have various pH levels in the range of 3 to 12 depending on the type of surfactant used. The pH is, for example, but not limited to, preferably 3 to 8, and more preferably 4 to 7. The pretreatment liquid may contain a preservative, a bactericide, a pH adjuster, a stabilizer, or the like as long as the effect of the present invention is not impaired.

(b) Staining Liquid

The staining liquid is used to stain the blotting membrane treated in step 2. When biofilm is present on the wound surface, biofilm components are adsorbed on the surface of the blotting membrane obtained in step 1. By the staining treatment with the staining liquid, the biofilm components can be stained while being adsorbed on the blotting membrane.

Examples of the dye include cationic dyes that selectively bind to anionic extracellular polysaccharides, particularly acidic mucopolysaccharides, present in the extracellular matrix of biofilm, and that have saturation, chromaticity, and hue so that the stained biofilm extracellular polysaccharides can be directly observed with the naked eye. Examples of dyes that have been used to stain biofilm include crystal violet and congo red (see, for example, Karsten Pedersen, Applied and Environmental Microbiology, January 1982, pp. 6-13; Bradford Craigen et: al., The Open Microbiology Journal, 2011, 5 21-31; and Masaaki Morikawa, "Let's examine biofilm," Biotechnology, Vol. 90, No. 5, pp. 246-250, 2012), as well as ruthenium red and alcian blue (see, for example, NPL 2 to NPL 4). Preferred are ruthenium red and alcian blue, and more preferred is alcian blue in terms of the stability after being prepared as an aqueous solution. Alcian blue is a basic dye belonging to phthalocyanine dyes, and has a positively-charged isothiouronium group as a functional group, which is known to be ionic bonded to the carboxyl group (—COO$^-$ group) or/and sulfate group (—SO$_4^-$ group) of acidic muco substances in the living body to stain blue the acidic muco substances. All of these dyes are commercially available.

The staining liquid is preferably used in the form of an aqueous solution in which the dye mentioned above is dissolved in water. The water used herein is not particularly limited, and examples include tap water, distilled water, ion-exchanged water, purified water, sterile water, and the like. The dye concentration of the staining liquid can be appropriately selected from the range of 0.05 to 1.2 mass %, as shown in Verification Experiment 2 described later. The lower limit value is preferably 0.1 mass % or more, for example. Further, the upper limit value is preferably 1 mass % or less, and more preferably 0.6 mass % or less, for example. It is not necessary to adjust the pH of the staining liquid with an acid, such as acetic acid or hydrochloric acid. The dye can be dissolved in water at a pH of 1 to 5, for example. The pH is, for example, but not limited to, preferably 2 to 5, and more preferably 2 to 4.5. The staining liquid may contain a preservative, a bactericide, a pH adjuster, a stabilizer, or the like as long as the effect of the present invention is not impaired.

(c) Decolorizing Liquid

The decolorizing liquid is used to decolorize the blotting membrane stained in step 3. The dye non-specifically attached to the blotting membrane can be desorbed by the treatment with the decolorizing liquid. On the other hand, the dye attached to the biofilm components adsorbed on the blotting membrane is specifically adsorbed to the biofilm components. Thus, this dye is not desorbed even by treatment with the decolorizing liquid; or, even if it is desorbed, the desorbing is slight, and the stained state can be maintained (coloring). That is, by the decolorization treatment with the decolorizing liquid, the dye attached to the biofilm component non-adsorbed portion of the blotting membrane is removed, and this membrane region undergoes color fading. In contrast, the biofilm components adsorbed on the surface of the blotting membrane are specifically bonded (ionic bonded) to the dye to maintain the stained state (coloring); thus, a contrast is made in comparison with the background color of the membrane, and the biofilm components adsorbed on the blotting membrane can be clearly visualized by the contrast image.

The decolorizing liquid comprises at least one surfactant selected from the group consisting of nonionic surfactants, amphoteric surfactants, and cationic surfactants. The nonionic surfactant, amphoteric surfactant, and cationic surfactant are not particularly limited as long as the effect of the present invention can be achieved; however, specific examples include the same as the surfactants for the pretreatment liquid described above. Therefore, the description relating to the pretreatment liquid can be incorporated here.

Nonionic surfactants are preferable because they exhibit stable effects in a relatively wide range of concentrations. Preferred among these are POE lauryl ether, polyoxyalkylene alkyl ether, and polyoxyethylene sorbitan fatty acid esters typified by polysorbate 80. According to these nonionic surfactants, as shown in Verification Experiment 1 described later, after the decolorization treatment, the biofilm component non-adsorbed region of the membrane further undergoes color fading as the blotting membrane dries, and the contrast with the colored portion due to the biofilm components becomes clearer, resulting in an effect of increasing the detection sensitivity and accuracy.

The decolorizing liquid is preferably used in the form of an aqueous solution in which such a surfactant is dissolved in water. The water used herein is not particularly limited, and examples include tap water, distilled water, ion-exchanged water, purified water, sterile water, and the like. The concentration of the surfactant in the decolorizing liquid can be appropriately selected from the range of 0.001 to 20 mass %, as shown in Verification Experiment 1 described later. The lower limit value is, for example, preferably 0.005 mass % or more, and more preferably 0.01 mass % or more. The upper limit value is preferably 10 mass % or less. Further, as shown in Verification Experiment 1, the pH of the decolorizing liquid does not make a significant difference in effectiveness, and the decolorizing liquid can have various pH levels in the range of 3 to 12 depending on the type of surfactant used. The pH is, for example, but not limited to, preferably 3 to 8, and more preferably 4 to 7. The decolorizing liquid may contain a preservative, a bactericide, a pH adjuster, a stabilizer, or the like as long as the effect of the present invention is not impaired.

As the decolorizing liquid, a reagent having the same composition as the pretreatment liquid described above can be preferably used. That is, in this case, it can be said that the pretreatment liquid also serves as the decolorizing liquid, while the decolorizing liquid also serves as the pretreatment liquid.

These pretreatment liquid, staining liquid, and decolorizing liquid constitute a part or all of the reagent kit in a state of being contained in separate containers. The material and shape of these containers are not particularly limited as long as the pretreatment liquid, staining liquid, and decolorizing liquid can be stably stored in a state in which they are contained therein without deterioration (including discoloration) or adsorption to the internal surface (if any). Examples of the material include, without limitation, glass, metal (e.g., aluminum, stainless steel, and steel), and plastic (e.g., polyethylene, polypropylene, polyethylene terephthalate, vinyl chloride, polystyrene, ABS resin, acrylic, polyamide, polycarbonate, and ethylene tetrafluoride). Further, the shape of the containers can be freely selected without particular limitation; for example, the shape of the containers can be a bottle shape, a pouch shape, or a tube shape. The size of the containers also depends on the amount of the pretreatment liquid, staining liquid, and decolorizing liquid used at one time, and on whether the reagent kit is used for one-time use (disposable) or multiple-time use. For example, when the reagent kit is for one-time use (disposable), the volume of the containers containing the pretreatment liquid, the staining liquid, and the decolorizing liquid is not particularly limited as long as the amount of each reagent used at one time can be contained. For example, the volume of the containers can be appropriately selected from the range of 2 to 20 mL. When the reagent kit is for multiple-time use, the size of the containers containing the pretreatment liquid, the staining liquid, and the decolorizing liquid can be appropriately selected according to the number of times of use. Although it is not limited, the volume of the containers can be appropriately selected from the range of 100 to 500 mL, for example. In the case of multiple-time use, it is particularly preferable that these containers have a lid that can be opened and closed. Further, in the case of multiple-time use, the containers may have a weighing scale, or may be equipped with a metering polar or a metering dispenser. When the pretreatment liquid and the decolorizing liquid have the same composition, the reagent kit may contain the pretreatment liquid and the decolorizing liquid in the same container. That is, in this case, the reagent kit is configured to have at least the "pretreatment liquid" and "decolorizing liquid" contained in one container and the "staining liquid" contained in another container.

The reagent, kit may have at least the three types of reagents, i.e., the pretreatment liquid, the staining liquid, and the decolorizing liquid, as a basic set, but may also contain a blotting membrane in addition to these reagents.

Blotting Membrane

The blotting membrane is used to collect biofilm components from the wound surface, and is then subjected to treatment with each of the above reagents. The blotting membrane may be a sheet (membrane) made of a material that adsorbs biofilm and/or components thereof (biofilm components) on one side of its surface. Examples include porous sheets (including, for example, non-woven fabrics) made of various fibrous materials. The blotting membrane is used in such a manner that it is attached to the skin surface (wound surface), including the target wounded area in which biofilm is to be detected, in a dry state as is or in a wet state with sterile water if necessary, left as is for several seconds to several tens of seconds, preferably about 10 seconds, and then peeled off. In this way, if biofilm is present on the wound surface, biofilm components can be adsorbed and collected on the contact surface of the blotting membrane. Therefore, it is preferable that the fibrous material and fiber structure of the blotting membrane can adsorb biofilm components by blotting described above. It is more preferable that the membrane has a fibrous material and a fiber structure capable of stably adsorbing and retaining biofilm components even in the subsequent pretreatment step, staining step, and decolorization step. It is even more preferable that the membrane has a fibrous material and a fibrous structure in which the staining liquid (dye) non-specifically attached to the membrane in the staining step after the pretreatment step can be easily desorbed (dropped off) by the decolorizing liquid in the subsequent decolorization step.

Examples of fibrous materials include, but are not limited to, as shown in Verification Experiment 3 described later, cellulose-based fibers, such as nitrocellulose, cellulose mixed ester, and cellulose acetate; nylon (including non-charged nylon and positive nylon); and hydrophilic fluororesin-based fibers, such as hydrophilic polyvinylidene difluoride (hydrophilic PVDF) and hydrophilic polytetrafluoroethylene (hydrophilic PTFE). The results of Verification Experiment 3 reveal that although blotting membranes can be used with or without charge, polar materials or highly hydrophilic fibrous materials can be preferably used.

The pore size of the blotting membrane is not limited, but is, for example, 0.1 to 0.5 μm, and preferably 0.2 to 0.45 μm. The thickness of the blotting membrane is also not particularly limited, but can be appropriately selected from the range of 0.05 to 1 mm, and preferably 0.05 to 0.3 mm, from the viewpoint of handling.

In the reagent kit, the shape of the blotting membrane is not particularly limited. For example, the blotting membrane may have a roll shape so that it can be cut into a desired shape and size at the time of use, or it may have a pre-cut shape (e.g., a rectangle). In terms of convenience of use, the blotting membrane is preferably pre-cut. The cut size is not particularly limited. For example, in the case of a rectangle, the size can be appropriately selected from the ranges of 3 to 30 cm in length and 3 to 30 cm in width. The blotting membranes may be packaged, in a sterilized state, in a bag one by one or together. Alternatively, the blotting membrane may be packaged in an airtight bag in a state of being infiltrated with sterile water or the like in advance.

The reagent kit may also comprise an instruction manual or a document describing a method for evaluating test results (evaluation of biofilm detection) or subsequent (recommended) treatment methods. Further, the reagent kit may also optionally have an auxiliary device for using the reagent kit, such as an immersion container, a draining member, a waste liquid saucer (waste liquid container), a container with a drainer, tweezers, sterile distilled water, or a drying device such as a dryer. The container with a drainer may be one having a draining member and a waste liquid container that are integrated, or one having a draining member and a waste liquid container that are detachably paired. The container with a drainer may have a lid so that it can be left or carried with the treated membrane placed on the drainer surface, for example. The draining member, the container with a drainer, the method for handling the reagent kit, the method for evaluating the test, results visualized on the blotting membrane, and the subsequent treatment based on the results will be described below.

The reagent kit can be suitably used for the detection of biofilm in wounds, as test tissue, for which the presence of biofilm is a particular concern, such as wounds with signs of clinical infection (inflammation, increased exudate, delayed healing, abscess formation, wound surface discoloration, granulation tissue formation, wound rupture, wound bottom pocket formation, foul odor, etc.), and refractory wounds, including chronic wounds, such as pressure ulcers, leg ulcers, and diabetic foot ulcers. The reagent kit can also be suitably used for the detection of biofilm in acute wounds (cuts, scratches, burns, etc.). The reagent kit can be used at the time of medical examination or when changing bandages or adhesive plasters at the bedside because of its ease of handling and quick result determination. Based on the results, treatment can be performed on the spot or a treatment plan can be made.

3. Biofilm Detection Method

The biofilm detection method of the present invention basically comprises step 1 (biofilm component collection step), step 2 (blotting membrane pretreatment step), step 3 (staining step), and step 4 (decolorization step) described above. If necessary, the biofilm detection method of the present invention may comprise step 5 (biofilm detection and determination step) after these steps.

(1) Step 1 (Biofilm Component Collection Step)

Step 1 has an operation of bringing a membrane capable of adsorbing biofilm components into contact with test tissue. Examples of the membrane used in this step include the blotting membrane described in section 2 above. It is preferable that the membrane is previously moistened with sterile water or the like before being brought into contact with the test tissue. By doing so, the pain in the affected area due to contact with the membrane is relieved, and biofilm components are easily attached and adsorbed on the membrane.

The target test tissue is a wound for which the possibility of the presence of biofilm is a concern, as described above. Preferred examples include wounds with signs of clinical infection (inflammation, increased exudate, delayed healing, abscess formation, wound surface discoloration, granulation tissue formation, wound rupture, wound bottom pocket formation, foul odor, etc.), and refractory wounds. For example, chronic wounds, such as pressure ulcers, leg ulcers, and diabetic foot ulcers, have an extremely high risk of developing infections, and thus can be suitable as the test tissue. Acute wounds (cuts, scratches, burns, etc.) for which the possibility of the presence of biofilm is a concern may also be used. The test tissue is preferably pretreated, for example, by washing with distilled water or physiological saline, in advance before being brought into contact with the membrane.

Contact of the membrane with the test tissue is not limited, but can be achieved by attaching the membrane to the surface (wound surface) of the test tissue. The attachment time is not limited, but is several seconds to several tens of seconds, for example, 5 seconds or more, preferably 10 seconds or more, and particularly preferably about 10 seconds. If necessary, the surface of the membrane attached to the wound surface may be lightly pressed during the attachment time so that biofilm components that can be present in the test tissue can be easily attached or adsorbed on the membrane. After the contact, the biofilm components can be collected on the membrane by removing the membrane from the test tissue. In other words, a membrane with a surface on which biofilm components collected from the test tissue are adsorbed can be prepared by the operation in step 1.

(2) Step 2 (Blotting Membrane Pretreatment Step)

Step 2 has an operation of pretreating, with a pretreatment liquid, the membrane with a surface on which biofilm components are adsorbed obtained in step 1. This step can prevent the dye from being non-specifically attached and fixed to the membrane (coloring). Examples of the pretreatment liquid used in this step include the pretreatment liquid described in section 2 above.

Figure 2:
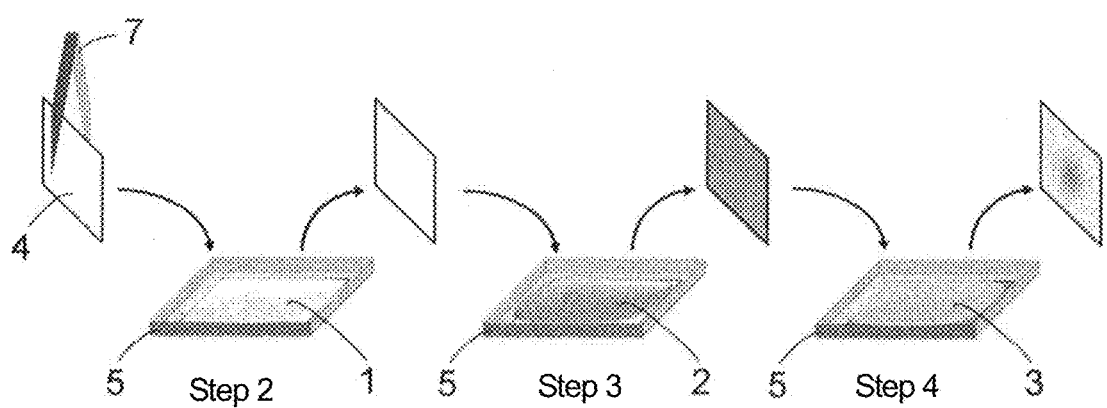
FIG. 2 is a schematic diagram showing another embodiment of step 2 (pretreatment step), step 3 (staining step), and step 4 (decolorization step) in the biofilm detection system of the present invention.
Figure 3:
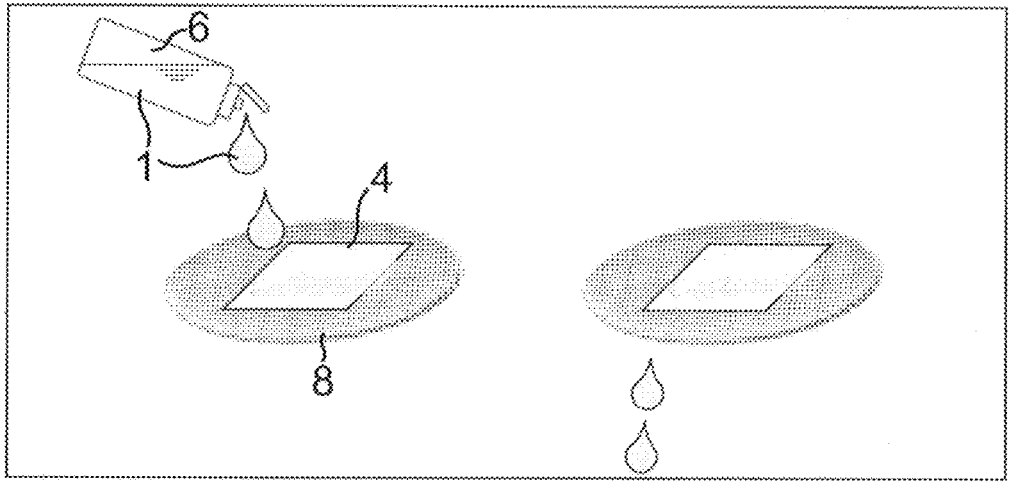
FIG. 3 is a schematic diagram showing still another embodiment of (1) step 2 (pretreatment step), (2) step 3 (staining step), and (3) step 4 (decolorization step) in the biofilm detection system of the present invention.
Figure 3:
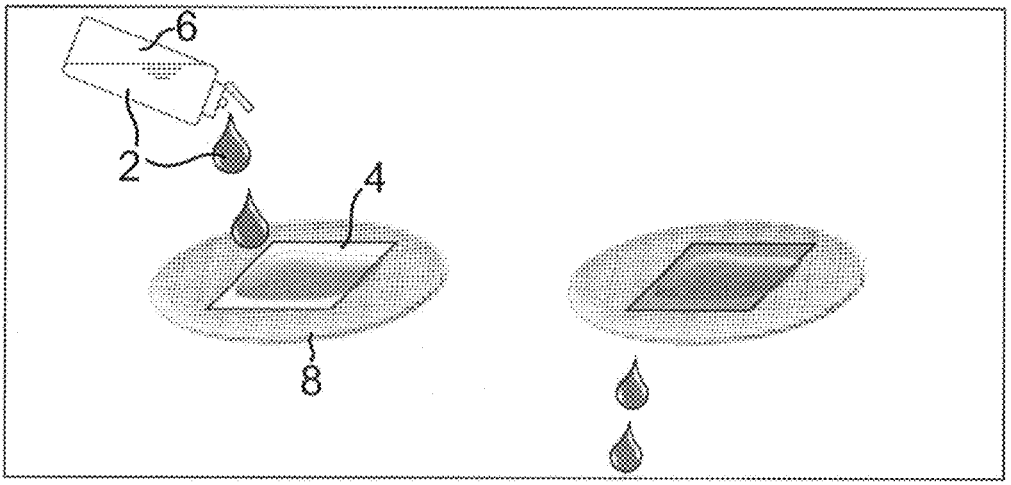
Figure 3:
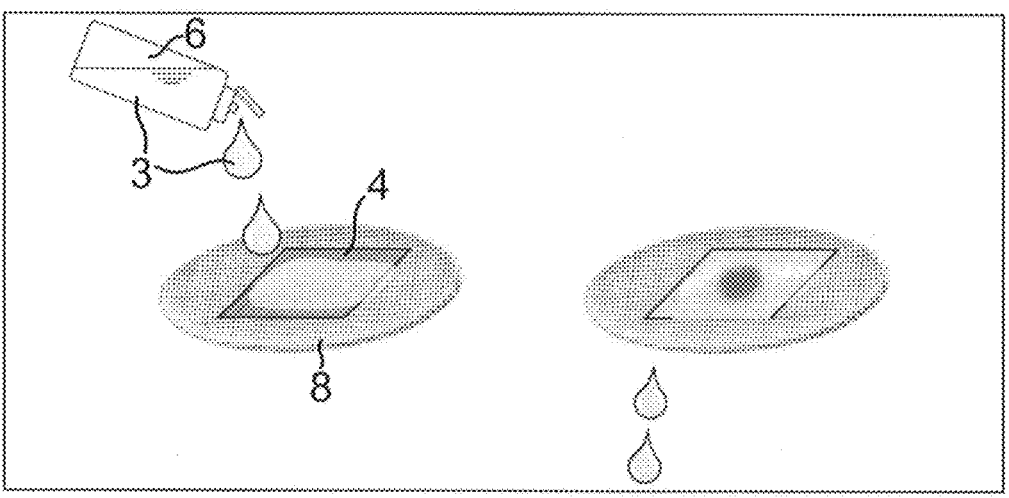
Figure 4:
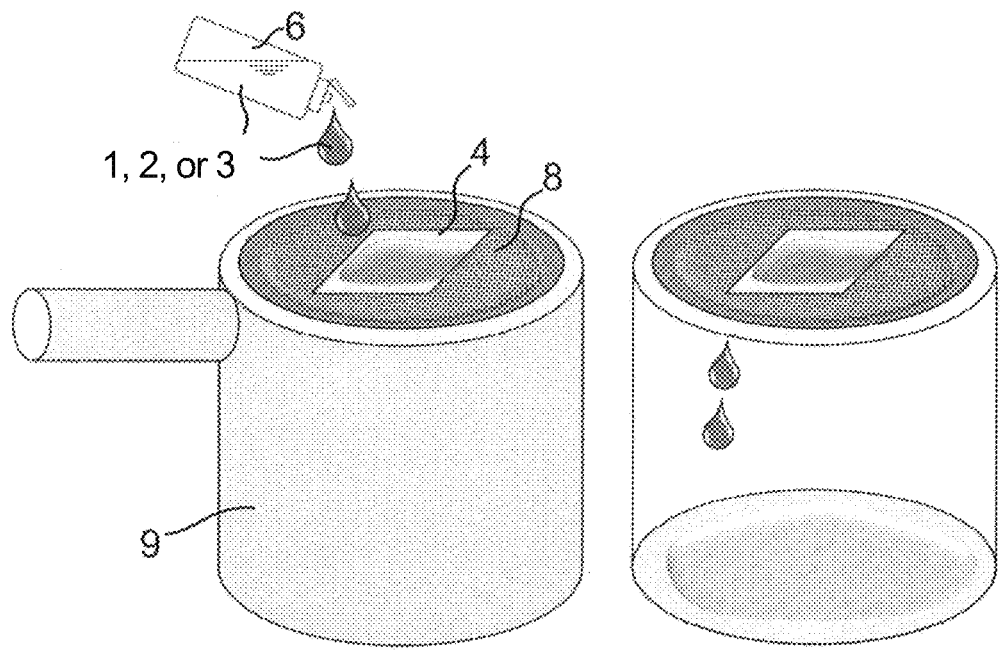
FIG. 4, views (1) and (2) both show embodiments of a draining member (sign 8) and a waste liquid container (sign 9) used in the biofilm detection system shown in FIG. 3.
Figure 4:
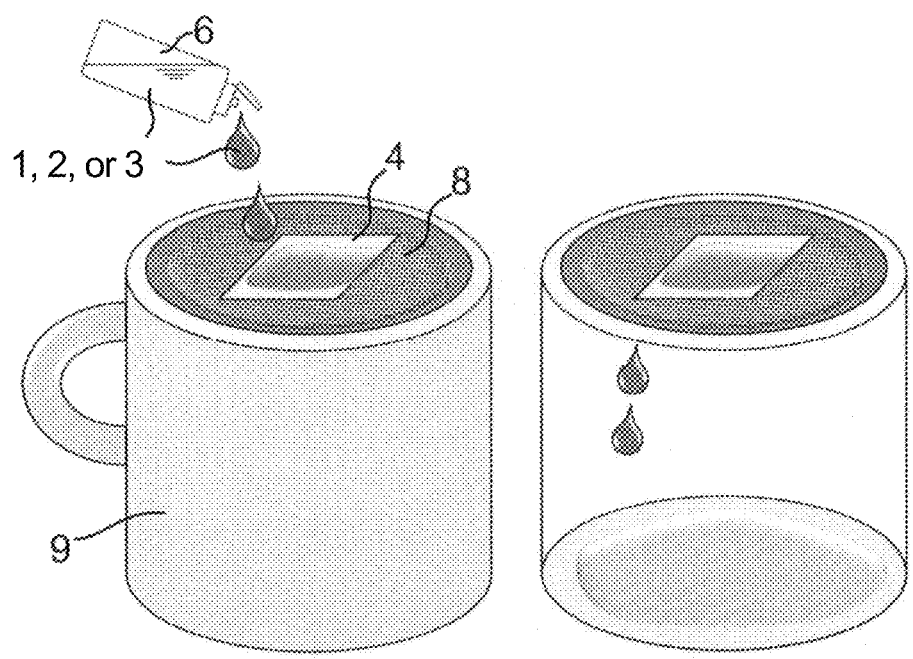

The treatment of the membrane with the pretreatment liquid may be a treatment (wet treatment) in which the pretreatment liquid is brought into contact with the entire membrane so that the membrane is soaked and moistened with the pretreatment liquid. The specific treatment operation is not particularly limited to this extent. For example, as shown in FIG. 1 (1), the membrane (sign 4) removed from the test tissue in step 1 is placed in a container (e.g., a tray) (sign 5), and in that state, the pretreatment liquid (sign 1) is placed in the container (sign 5) so that the entire membrane is immersed and moistened with the pretreatment liquid (immersion method); as shown in FIG. 2, the membrane (sign 4) is placed in a container (e.g., a tray) (sign 5) containing the pretreatment liquid (sign 1) in advance, and immersed and moistened with the pretreatment liquid (immersion method); or the pretreatment liquid is sprayed or dropped onto the membrane removed from the test tissue in step 1 to spread evenly for moistening (spraying or dropping method). When the spraying or dropping method is used, as shown in FIG. 3 (1), this method can be carried out while the membrane (sign 4) is placed on a member with an opening, such as a net (in the present invention, this is referred to as "draining member") (sign 8). The material, shape, size, etc., of the draining member are not particularly limited, and any member can be used as long as it can hold the membrane spread on its top and has an opening (liquid passage hole) that allows the passage of an excess amount of the pretreatment liquid more than the amount used for moistening the membrane. For example, the flat plate-like member (sheet- or plate-like member) shown in FIG. 3 (1), a colander (semi-circular or hollow-shaped draining container) with a handle, such as a scum, remover or a tea strainer, and something like a powder sieve can also be used without distinction. In that case, as shown in FIG. 4 (1) and (2), a saucer or container for containing the passing pretreatment liquid (hereinafter referred to as "waste liquid container") (sign 9) is placed under the draining member (sign 8), whereby the pretreatment liquid can be collected as waste liquid therein. It is also possible to use a container with a drainer, in which a draining member and a waste liquid container are detachably paired. The shape and size of the opening (liquid passage hole) of the draining member are not particularly limited as long as the above object can be achieved. The wet treatment time is not limited, but is, for example, in the range of 2 to 60 seconds under room temperature conditions (25±5° C.). The wet treatment time is preferably 2 to 30 seconds, and more preferably 2 to 15 seconds. After the wet treatment with the pretreatment liquid, the pretreatment liquid is removed from the container (see FIG. 1 (1)), the treated membrane is removed from the container containing the pretreatment liquid (see FIG. 2), or while leaving the membrane placed on the draining member, an excess amount of the pretreatment liquid is dropped from the opening of the draining member by its own weight (by tilting the draining member, if necessary) (see FIG. 3 (1)), and collected as waste liquid in the waste liquid container (sign 9) (see FIG. 4). In this manner, step 2 can be completed.

In step 2, the amount of the pretreatment liquid used for one wet treatment is not particularly limited as long as the wet treatment can be achieved. Although it depends on the size of the target test tissue and the size of the membrane used, for example, when the membrane is a 5 cm×5 cm rectangular sheet, the amount of the pretreatment liquid is 2 to 10 mL per treatment, for example. Although the number of times of wet treatment is not limited, one treatment is generally sufficient.

(3) Step 3 (Blotting Membrane Staining Step)

Step 3 has an operation of staining the membrane (pretreated membrane) obtained in step 2. This step can stain the biofilm components adsorbed on the membrane in a state of being adsorbed on the membrane. Examples of the staining liquid used in this step include the staining liquid described in section 2 above.

The treatment of the membrane with the staining liquid may be a treatment (wet treatment) in which the staining liquid is brought into contact with at least the biofilm component-adsorbed portion of the membrane pretreated with the pretreatment liquid (wet treatment) so that the membrane is soaked and moistened with the staining liquid. The specific treatment operation is not particularly limited to this extent. For example, as shown in FIG. 1 (2), the staining liquid (sign 2) is placed in the membrane-containing container (sign 5), from which the pretreatment liquid has been removed in step 2, so that the entire membrane (sign 4) is immersed and infiltrated in the staining liquid (immersion method); as shown in FIG. 2, the membrane taken out of the container (sign 5) containing the pretreatment liquid (sign 1) is placed in a container (sign 5) containing the staining liquid (sign 2) so that the membrane is immersed and infiltrated in the staining liquid (immersion method); or the membrane pretreated in step 2 is moistened by spraying or dropping the staining liquid (spraying or dropping method). When the spraying or dropping method is used, as shown in FIG. 3 (2), the method can also be carried out while the membrane (sign 4) is placed on the draining member (sign 8) in the same manner as in the pretreatment step (or continuous from the pretreatment step). Also in this case, as in the pretreatment step (or continuous from the pretreatment step), as shown in FIG. 4 (1) and (2), a waste liquid container (sign 9) is placed under the draining member (sign 8), whereby the staining liquid can be collected as waste liquid, in the same manner as the pretreatment liquid. Since the staining liquid used in the present invention does not generate heat or react even when mixed with the pretreatment liquid described above, the staining liquid can be stored as waste liquid in the waste liquid container used in step 2, while the pretreatment liquid is stored therein. The wet treatment time (staining time) with the staining liquid is not limited, but is, for example, in the range of 5 to 60 seconds under room temperature conditions (25±5° C.). The wet treatment time is preferably 10 to 60 seconds, and more preferably 10 to 30 seconds. After the wet treatment (staining treatment) with the staining liquid, the staining liquid is removed from the container (see FIG. 1 (2)), the treated membrane is removed from the container containing the staining liquid (see FIG. 2), or while leaving the membrane as is, an excess amount of the staining liquid is dropped from the opening of the draining member by its own weight (by tilting the draining member, if necessary) (FIG. 3 (2)), and collected as waste liquid in the waste liquid container (see FIG. 4). In this manner, step 3 can be completed.

In step 3, the amount of the staining liquid used for one wet treatment (staining treatment) is not particularly limited as long as the wet treatment (staining treatment) can be achieved. Although it depends on the size of the target test tissue and the size of the membrane used, for example, when the membrane is a 5 cm×5 cm rectangular sheet, the amount of the staining liquid is 2 to 10 mL per treatment, for example. Although the number of times of wet treatment (staining treatment) is not limited, one treatment is generally sufficient.

(4) Step 4 (Blotting Membrane Decolorization Step)

Step 4 has an operation of decolorizing the membrane (stained membrane) obtained in step 3. This step can desorb the dye non-specifically attached to the membrane, while the coloring of the biofilm components adsorbed on the membrane remains. As a result of thus reducing the coloring of the background membrane itself (color fading), the presence of the biofilm components adsorbed on the membrane can be highlighted as a contrast image, which allows visual and easy confirmation (visualization of biofilm). Examples of the decolorizing liquid used in this step include the decolorizing liquid described in section 2 above. Preferably, a reagent having the same composition as the pretreatment liquid used in step 2 can be used.

The treatment of the membrane with the decolorizing liquid may be a treatment (wet treatment) in which the decolorizing liquid is brought into contact with the membrane area that has been subjected to wet treatment (staining treatment) with the staining liquid so that the membrane is soaked and moistened with the decolorizing liquid. The specific treatment operation is not particularly limited to this extent. For example, as shown in FIG. 1 (3), the membrane-containing container (sign 5) from which the staining liquid has been removed in step 3 is washed, if necessary, and the decolorizing liquid (sign 3) is placed therein so that the entire membrane is immersed and moistened with the decolorizing liquid (immersion method); as shown in FIG. 2, the membrane taken out from the container (sign 5) containing the staining liquid (sign 2) is placed in a container (sign 5) containing the decolorizing liquid (sign 3) so that the membrane is immersed and moistened with the decolorizing liquid (immersion method); or the membrane stained in step 3 is moistened by spraying or dropping the decolorizing liquid (spraying or dropping method). When the spraying or dropping method is used, as shown in FIG. 3 (3), the method can be carried out while the membrane (sign 4) is placed on a draining member (sign 8), as in the pretreatment step and the staining step (or continuous from the pretreatment step and the staining step). Also in this case, as in the pretreatment step and the staining step (or continuous from the pretreatment step and the staining step), as shown in FIG. 4 (1) and (2), a waste liquid container (sign 9) is placed below the draining member (sign 8), whereby the decolorizing liquid can be collected as waste liquid therein, in the same manner as the pretreatment liquid and the staining liquid. Since the decolorizing liquid used in the present invention does not generate heat or react even when mixed with the pretreatment liquid and staining liquid described above, the decolorizing liquid can be stored as waste liquid in the waste liquid container used in steps 2 and 3, in which the pretreatment liquid and staining liquid are stored. The wet treatment time (decolorizing time) with the decolorizing liquid is not limited, but is, for example, in the range of 10 to 120 seconds under room temperature conditions (25±5° C.). The wet treatment time is preferably 10 to 60 seconds, and more preferably 10 to 30 seconds. After the wet treatment (decolorization treatment) with the decolorizing liquid, the decolorizing liquid is removed from the container (see FIG. 1 (3)), the treated membrane is removed from the container containing the decolorizing liquid (see FIG. 2), or while leaving the membrane as is, an excess amount of the decolorizing liquid is dropped from the opening of the draining member by its own weight (by tilting the draining member, if necessary) (FIG. 3 (3)), and collected as waste liquid in the waste liquid container (see FIG. 4). In this manner, step 4 can be completed.

In step 4, the amount of the decolorizing liquid used for one wet treatment (decolorization treatment) is not particularly limited as long as the wet treatment (decolorization treatment) can be achieved. Although it depends on the size of the target test tissue and the size of the membrane used, for example, when the membrane is a 5 cm×5 cm rectangular sheet, the amount of the decolorizing liquid is 2 to 10 mL per treatment, for example. Although the number of times of wet treatment (decolorization treatment) is not limited, one treatment is generally sufficient.

The series of operations of steps 1 to 4 can be performed continuously, but can also be performed discontinuously as long as the effect of the present invention can be obtained. When the series of operations of steps 1 to 4 are continuously performed, the total time required is the sum of the times required for the respective steps, and is preferably within 2 minutes, for example. In the case of performing steps 1 to 4 discontinuously, for example, the membrane prepared in step 1 may be stored until it is subjected to step 2, or the membrane pretreated in step 2 may also be stored until it is subjected to step 3 (staining step).

(5) Step 5 (Biofilm Detection and Determination Step)

The presence of biofilm components adsorbed on the membrane can be confirmed by visually observing the colored state of the decolored membrane obtained in step 4. Specifically, if the contact surface with the test tissue of the membrane obtained in step 4 makes a contrast with the background color (light color) of the membrane due to coloring with the dye used in step 3, assuming that biofilm components are adsorbed on the membrane, it can be determined that biofilm is present on the target test tissue. On the other hand, if no contrast is made on the membrane obtained in step 4, assuming that biofilm components are not adsorbed on the membrane, it can be determined that biofilm is not present on the target test tissue. The determination by such visualization can be made immediately after the decolorization treatment, but is not limited thereto; the determination can be made even after the membrane has dried. In particular, when pretreatment and decolorization treatment are performed using, as the pretreatment liquid and decolorizing liquid, an aqueous solution containing at least one nonionic surfactant selected from the group consisting of POE lauryl ether, polyoxyalkylene alkyl ether, and polyoxyethylene sorbitan fatty acid esters typified by polysorbate 80, the color fading of the background color of the membrane becomes more remarkable by drying the membrane after the decolorization treatment. As a result, the contrast becomes clearer and the biofilm components can be highlighted and visualized. Therefore, if is possible to provide a step of drying the membrane after the decolorization step and before the detection and determination step.

Such coloring in the membrane, to be precise, detection of biofilm components using the contrast (contrast image) to the background color of the membrane as an index, and decision (determination) of the presence of biofilm in the test tissue based on the detection of biofilm components can be easily carried out by using the membrane obtained by the treatments of steps 1 to 4 or, if necessary, the subsequent drying treatment. Therefore, according to the biofilm detection method of the present invention, particularly the biofilm detection method using the reagent kit of the present invention, anyone, not just a doctor, can easily determine the presence of biofilm in the test tissue. The detection and determination of biofilm in the test tissue using the reagent kit or detection method of the present invention (the biofilm detection system of the present invention) can be used for definitive diagnosis of the presence of biofilm in raw tissue, as well as for auxiliary or pre-diagnosis of conventional tissue biopsy and/or microscopic observation.

If it is determined by the method of the present invention that biofilm is present in the test tissue, it is preferable to remove the biofilm from the test tissue and, if necessary, take further measures to prevent the reformation of biofilm. Such measures may be carried out consecutively after the biofilm detection method of the present invention, or may be carried out after the proposal and examination as one of the treatment methods. Although the method for removing biofilm is not limited, examples of conventional methods include physical destruction (aggressive/sharp debridement) and physical cleaning (cleaning or sonication). Further, examples of the method for preventing biofilm reformation include methods of preventing further wound infections by killing microorganisms with dressing materials (e.g. silver dressing materials, iodine dressing materials, PHMB dressing materials, and medical honey dressing materials), topical broad-spectrum antibiotics, or surfactants (see NPL 1 etc.).

In the present specification, the term "comprise" or "contain" includes the meanings of "consisting of" and "substantially consisting of."

EXAMPLES

The structure and effect of the present invention are described below based on experimental examples. However, the experimental examples are merely examples for explaining the present invention, and the present invention is not limited by these experimental examples. In the following, unless otherwise specified, "%" means "mass %" find "part" means "part by mass." Further, unless otherwise specified, the experiments were carried out under atmospheric pressure conditions in a room adjusted to a constant temperature (25±2° C.) and humidity (35±15%).

Experimental Example 1: Design of Biofilm Detection System and Verification

A biofilm detection system comprising the following steps 1 to 5 was designed by applying wound blotting, and a pretreatment liquid used in step 2, a staining liquid used in step 3, a decolorizing liquid used in step 4, and a blotting membrane used in steps 1 to 5 were verified.
Step 1: Biofilm component collection step
Step 2: Pretreatment step (for blotting membrane)
Step 3: Staining step (for blotting membrane)
Step 4: Decolorization step (for blotting membrane)
Step 5: Biofilm detection and determination step Step 1: Biofilm Collection Step (Required Time: About 10 Seconds)

Step 1 is a step of attaching a blotting membrane to a wound surface so that biofilm components present on the wound surface are adsorbed on the membrane. By this step, if biofilm is present on the wound surface, biofilm components can be collected on the blotting membrane.

In Verification Experiments 1 to 3 below, instead of the step of attaching a blotting membrane to a wound surface to adsorb biofilm components, a *Pseudomonas aeruginosa* biofilm suspension ($10^7$ to $10^9$ CFU/mL) prepared in the following manner was dropped (2 μL, 10 μL) on the surface of a blotting membrane (5 cm×5 cm rectangular sheet) previously moistened with sterile water, thereby allowing biofilm components to be adsorbed on the blotting membrane. The colonies (including extracellular substances) used in the biofilm suspension were collected with a platinum loop and attached to a hard (glass) surface, and a 0.1% crystal violet aqueous solution was added for staining for about 20 minutes, followed by gentle washing with water a few times. Then, staining was confirmed.

Method for Preparing Biofilm Suspensions of *Pseudomonas aeruginosa* and *Staphylococcus aureus*

Evaluation was performed using *Pseudomonas aeruginosa* PAO1 strain, ATCC 15442, and ATCC 27853 as *Pseudomonas aeruginosa*, and *Staphylococcus aureus* ATCC 29213 as *Staphylococcus aureus*. *Pseudomonas aeruginosa* and *Staphylococcus aureus* were each cultured on a tryptic soy broth-agar medium at 37° C. for 48 hours. Colonies (including extracellular substances) generated by culture were collected with sterile water, and were each adjusted to $10^7$ to $10^9$ CFU/mL. These were used as biofilm suspensions in Verification Experiments 1 to 3 below.

Step 2: Blotting Membrane Pretreatment Step (Required Time: 2 to 60 Seconds)

Step 2 is a step of treating, with a pretreatment liquid, the blotting membrane with biofilm components adsorbed thereon. This step can prevent coloring of the membrane portion on which no biofilm components are adsorbed.

In Verification Experiments 1 to 3 below, first the blotting membrane treated in step 1 was placed in a container for immersion treatment (7 cm×7 cm, 1 cm-high plate-like container). Hereinafter, step 2 and subsequent steps 3 and 4 were all performed in this container. The outline is shown in FIG. 1 (1). Specifically, 2 to 10 mL of pretreatment liquid (sign 1) was added to a container (sign 5) containing a blotting membrane (sign 4), the blotting membrane was immersed in the pretreatment liquid for 30 seconds, and then the pretreatment liquid was removed from the container (see FIG. 1 (1)). In Experimental Example 4 (1) described later, step 2 was performed using the method shown in FIG. 2, and in Experimental Example 4 (2), step 2 was performed using the method shown in FIG. 3 (1). In Experimental Example 4 (1), specifically, a blotting membrane (sign 4) was placed in a container (sign 5) containing 2 to 10 mL of pretreatment liquid (sign 1) for immersion and moistening, and then the membrane was removed from the container (see FIG. 2). In Experimental Example 4 (2), specifically, a blotting membrane (sign 4) was placed on a draining member (sign 8), 2 to 10 mL of pretreatment liquid (sign 1) was evenly sprayed or dropped thereon to spread throughout the entire membrane (infiltration), and then an excessive amount of the pretreatment liquid was passed through the draining member (sign 8) (see FIG. 3 (1)), and collected as waste liquid in a waste liquid container placed under the draining member.

Step 3: Blotting Membrane Staining Step (Required Time: 5 to 60 Seconds)

Step 3 is a step of treating, with a staining liquid, the blotting membrane treated with the pretreatment liquid in step 2. This step can stain the blotting membrane, and also stain the biofilm components adsorbed on the surface of the blotting membrane.

In Verification Experiments 1 to 3 below, specifically, 2 to 10 mL of staining liquid (sign 2) was added to the container (sign 5) from which the pretreatment liquid (sign 1) had been removed in step 2, the blotting membrane was immersed in the staining liquid for 30 seconds, and then the staining liquid was removed from the container (see FIG. 1 (2)). In Experimental Example 4 (1) described later, step 3 was performed using the method shown in FIG. 2, and in Experimental Example 4 (2), step 3 was performed using the method shown in FIG. 3 (2). In Experimental Example 4 (1), specifically, the blotting membrane (sign 4) was placed in a container (sign 5) containing 2 to 10 mL of staining liquid (sign 2) for immersion and moistening, and then the membrane was removed from the container (see FIG. 2). In Experimental Example 4 (2), specifically, the blotting membrane (sign 4) was placed on a draining member (sign 8), 2 to 10 mL of staining liquid (sign 2) was evenly sprayed or dropped thereon to spread throughout the entire membrane (infiltration), and then an excessive amount of the staining liquid was passed through the draining member (sign 8) (see FIG. 3 (2)), and collected as waste liquid in a waste liquid container placed under the draining member.

Step 4: Blotting Membrane Decolorization Step (required Time: 10 to 120 Seconds)

Step 4 is a step of treating, with a decolorizing liquid, the blotting membrane treated with the staining liquid in step 3. This step can desorb the dye non-specifically attached to the blotting membrane stained in step 3. However, the dye specifically binding to the biofilm components adsorbed on the blotting membrane remains as is without desorption (coloring). As a result, the presence of the biofilm components adsorbed on the blotting membrane can be clearly confirmed visually (visualization of biofilm components).

In Verification Experiments 1 to 3 below, specifically, 2 to 20 mL of decolorizing liquid (sign 3) was added to the container (sign 5) from which the staining liquid (sign 2) had been removed in step 3, the blotting membrane was immersed in the decolorizing liquid for 60 seconds, and then the decolorizing liquid was removed from the container (see FIG. 1 (3)). In Experimental Example 4 (1) described later, step 4 was performed using the method shown in FIG. 2, and in Experimental Example 4 (2), step 4 was performed using the method shown in FIG. 3 (3). In Experimental Example 4 (1), specifically, the blotting membrane (sign 4) was placed in a container (sign 5) containing 2 to 10 mL of decolorizing liquid (sign 3) for immersion and moistening, and then the membrane was removed from the container (see FIG. 2). In Experimental Example 4 (2), specifically, the blotting membrane (sign 4) was placed on a draining member (sign 8), 2 to 10 mL of decolorizing liquid (sign 3) was evenly sprayed or dropped thereon to spread throughout the entire membrane (infiltration), then an excessive amount of the decolorizing liquid was passed through the draining member (sign 8) (see FIG. 3 (2)), and collected as waste liquid in a waste liquid container placed under the draining member.

Step 5: Biofilm Detection and Determination Step

Step 5 is a step of visually confirming the colored state of the blotting membrane treated with the decolorizing liquid in step 4. This step can determine whether biofilm is present on the wound surface to which the blotting membrane has been attached in step 1. When the contact surface with the wound surface of the blotting membrane treated with the decolorizing liquid is colored with the dye, and a contrast image with respect to the background color of the membrane is observed (positive detection), it can be determined that biofilm is present on the wound surface. Specifically, when biofilm is present on the wound surface, biofilm components are adsorbed on the contact surface of the blotting membrane with the wound surface; thus, the dye is not desorbed from the adsorbed portion even by the decolorization treatment after the staining treatment. Accordingly, the adsorbed portion is colored in a clearly darker color than the background color (light color) of the membrane from which the dye has been desorbed, and a contrast darker than the background color (light color) of the membrane is formed (contrast image).

The following verification experiments evaluated the presence of contrast images at 2 locations of the blotting membrane surface where the biofilm suspension was dropped.

Verification Experiment 1: Verification of Pretreatment Liquid and Decolorizing Liquid In Verification Experiment 1, aqueous solutions prepared by diluting the surfactants shown in Table 1 to various concentrations (0.001 to 20%) were used as the pretreatment liquid used in step 2 (pretreatment step) and the decolorizing liquid used in step 4 (decolorization treatment step), and the biofilm detection system (pretreatment: 30 seconds, staining treatment: 30 seconds, and decolorization treatment: 60 seconds; 2 minutes in total) was carried out to verify the practicality of the pretreatment liquid and decolorizing liquid. In this verification experiment, the blotting membrane used in step 1 was a nitrocellulose membrane with a pore size of 0.2 μm (trade name: Supported Nitrocellulose Membrane, Bio-Rad #1620097) cut into a rectangle of 5 cm×5 cm. The staining liquid used in step 3 (staining step) was a 0.3% alcian blue aqueous solution (pH: 4.0) prepared using Alcian Blue 8GX (A9186, Sigma-Aldrich).

After 1 minute of the decolorization treatment, the blotting membrane was taken out from the container, and the colored state (the presence of contrast images) was visually confirmed. The results are shown in Tables 1 and 2. Table 1 shows the results of using, as the biofilm suspension, a *Pseudomonas aeruginosa* PAO1 strain suspension (blotted with 10 μl of $10^9$ CFU/mL), and Table 2 shows the results of using, as the biofilm suspensions, *Pseudomonas aeruginosa* ATCC 15442, *Pseudomonas aeruginosa* ATCC 27853, and *Staphylococcus aureus* ATCC 29213 suspensions (blotted with 10 μl of $10^9$ CFU/mL). The evaluation criteria (○, Δ, x) shown in Tables 1 and 2 are as follows.

Evaluation Criteria

○: Contrast images could be visually confirmed immediately after decolorization.
Δ: Contrast images could not be visually confirmed immediately after decolorization; however, when the membrane dried, contrast images could be visually confirmed. x: Contrast images could not be visually confirmed immediately after decolorization or when the membrane dried.

TABLE 1

| | Type of surfactant | Final effective concentration of surfactant | | | | | | | | |
|---|---|---|---|---|---|---|---|---|---|---|
| | | 0.001% | 0.005% | 0.01% | 0.1% | 0.5% | 1% | 5% | 10% | 20% |
| Nonionic | (1) Polysorbate 80 | ○ | — | ○ | ○ | ○ | ○ | ○ | ○ | ○ |
| | (2) Polyoxyethylene lauryl ether | — | — | ○ | ○ | ○ | ○ | ○ | ○ | ○ |
| | (3) Polyoxyalkylene alkyl ether | — | — | Δ | — | ○ | ○ | ○ | ○ | — |
| | (4) Alkyl polyglycoside | — | Δ | — | ○ | — | — | — | — | — |
| | (5) Polyoxyethylene (3) polyoxypropylene glycol (17) | — | ○ | — | ○ | — | ○ | — | ○ | — |
| | (6) Decaglyceryl monocaprate | — | — | — | ○ | — | ○ | — | ○ | — |
| Amphoteric | (7) Lauryldimethylaminoacetic acid betaine | — | — | Δ | Δ | — | ○ | ○ | — | — |
| | (8) Lauryldimethylamine oxide | — | — | ○ | ○ | — | ○ | ○ | — | — |
| Cationic | (9) Didecyldimethyl ammonium chloride | — | Δ | — | ○ | — | — | — | — | — |
| | (10) Benzalkonium chloride | — | ○ | — | ○ | — | — | — | — | — |
| Anionic | (11) Na polyoxyethylene lauryl ether sulfate | — | — | — | x | — | x | x | — | — |
| | (12) Na dodecyl sulfate | — | — | — | x | — | — | x | — | — |
| | (13) Na linear alkylbenzene sulfonate | — | — | — | x | — | — | x | — | — |

In the table, "—" means non-implementation.
(1) Nonion OT-221: NOF Corporation, pH: 4.0 to 7.0
(2) Blaunon EL 1509: Aoki Oil Industrial Co., Ltd., pH: 4.5 to 7.0
(3) Emulgen MS110: Kao Corporation, pH: 4.0 to 7.0
(4) Triton CG-50 (containing 50% alkyl polyglycoside): The Dow Chemical Company, pH: 9.0 to 12.0
(5) Pluronic L-31: ADEKA Corporation, pH: 3.0 to 5.0
(6) Sunsoil Q10Y-C: Taiyo Kagaku Co., Ltd., pH: 3.0 to 6.0
(7) Rikabion A-100 (containing 30% lauryldimethylaminoacetic acid betaine): New Japan Chemical Co., Ltd., pH: 6.0 to 8.0
(8) Genaminox K-12 (containing 32% lauryldimethylamine oxide): Clariant Japan K. K., pH 6.0 to 8.0
(9) Cation DDC-80 (containing 80% didecyldimethyl ammonium chloride): Sanyo Chemical Industries, Ltd., pH: 5.0 to 7.0
(10) Cation F2-50 (containing 50.7% benzalkonium chloride): NOF Corporation, pH: 5.0 to 7.0
(11) Taycapol NE1230 (containing 27% Na polyoxyethylene lauryl ether sulfate): Tayca Corporation, pH: 4.0 to 5.0
(12) SDS: FUJIFILM Wako Pure Chemical Corporation, pH: 5.0 to 6.0
(13) LAS: FUJIFILM Wako Pure Chemical Corporation, pH: 6.0 to 7.0

TABLE 2

| Type of surfactant | Concentration of surfactant | Pseudomonas aeruginosa ATCC 15442 | Psounfornortas aeruginosa ATCC 27853 | Stephylococcus aureus ATCC 29213 |
|---|---|---|---|---|
| Nonionic | | | | |
| (1) Polysorbate 80 | 0.1% | ○ | ○ | ○ |
| | 1.0% | ○ | ○ | ○ |
| (2) Polyoxyethylene lauryl ether | 0.1% | ○ | ○ | ○ |
| | 1.0% | ○ | ○ | ○ |
| | 10.0% | ○ | ○ | ○ |
| (3) Polyoxyakylene alkyl ether | 1.0% | ○ | ○ | ○ |
| (5) Polyoxyethylene polyoxypropylene glycol | 1.0% | ○ | ○ | ○ |
| Ampholeric | | | | |
| (7) Lauryldimethylaminoacetic acid betaine | 1.0% | ○ | ○ | ○ |
| Cationic | | | | |
| (9) Didecyldimethyl ammonium chloride | 0.1% | ○ | ○ | ○ |
| Anionic | | | | |
| (11) Sodium polyoxyethylene lauryl ether sulfate | 1.0% | X | X | X |

Of the results shown in Table 1, FIG. 5 shows images showing the colored state (immediately after decolorization and after drying) of the blotting membranes that had been subjected to the pretreatment and the decolorization treatment using aqueous solutions containing, as a surfactant, any of (1) polysorbate 80, (2) polyoxyethylene lauryl ether, and (3) polyoxyalkylene alkyl ether (all nonionic surfactants), (7) lauryldimethylaminoacetic acid betaine and (8) lauryldimethylamine oxide (all amphoteric surfactants), and (11) sodium polyoxyethylene lauryl ether sulfate (anionic surfactant), at a concentration of 5%.

As shown in Tables 1 and 2, it was confirmed that the aqueous solutions containing a nonionic surfactant, an amphoteric surfactant, or a cationic surfactant at a concentration of 0.001 to 20% were useful as the pretreatment liquid and the decolorizing liquid. Further, as shown in FIG. 5, when the pretreatment and the decolorization treatment were carried out using the aqueous solutions containing a nonionic surfactant or an amphoteric surfactant, the presence of biofilm could be clearly visualized on the blotting membranes even immediately after the decolorization treatment, and that state was stably maintained even after the blotting membranes dried. Of these, for the aqueous solutions containing a nonionic surfactant, particularly (1) polysorbate 80, (2) polyoxyethylene lauryl ether, or (3) polyoxyalkylene alkyl ether, it was confirmed that stable results were obtained in a wide range of concentrations; and that, as the blotting membrane dried, the bluish and reddish color in the background of the membrane became pale (color fading), and the contrast with the colored portion where the biofilm components were adsorbed became clearer, thereby significantly visualizing the presence of biofilm on the blotting membrane.

In Verification Experiment 1, it was also confirmed that although steps 2, 3, and 4 were continuously performed, even when the blotting membrane pretreated in step 1 was left to dry under room temperature conditions for 1 week, and then the steps subsequent to step 2 were performed for staining and decolorization treatment, the presence of biofilm could be significantly visualized on the blotting membrane.

Verification Experiment 2: Verification of Staining Liquid

In Verification Experiment 2, aqueous solutions prepared by diluting the dyes (ruthenium red and alcian blue) shown in Table 2 to various concentrations (0.05 to 1.2%) were used as the staining liquid used in step 3 (staining step), and the biofilm detection system (pretreatment: 30 seconds, staining treatment: 30 seconds, and decolorization treatment: 60 seconds; 2 minutes in total) was carried out to verify the practicality of the staining liquids.

Each staining liquid was prepared in the following manner. The staining liquids were not prepared in advance, but were prepared just before this verification experiment was carried out.
(1) Ruthenium red aqueous solution
Ruthenium red powder (color index 77800) was dissolved in water to 0.5%.
(2) Alcian blue aqueous solution
Alcian blue powder (color index 74240) was dissolved in water to 0.05% to 1.2%.

In Verification Experiment 2, the blotting membrane used in step 1 was a nitrocellulose membrane with a pore size of 0.2 μm (trade name: Supported Nitrocellulose Membrane, Bio-Rad #1620097) cut into a rectangle of 5 cm×5 cm. The pretreatment liquid used in step 2 (pretreatment step) and the decolorizing liquid used in step 4 (decolorization step) were a 5% polyoxyethylene lauryl ether (Blaunon EL 1509, produced by Aoki Oil Industrial Co., Ltd.) aqueous solution.

After 1 minute of the decolorization treatment, the blotting membrane was taken out from the container, and the colored state was visually confirmed. The results are shown in Tables 3 and 4. Table 3 shows the results of using, as the biofilm suspension, a Pseudomonas aeruginosa PAO1 strain suspension (blotted with 10 μl of $10^9$ CFU/mL), and Table 4 shows the results of using, as the biofilm suspensions, Pseudomonas aeruginosa ATCC 15442, Pseudomonas aeruginosa ATCC 27853, and Staphylococcus aureus ATCC 29213 suspensions (blotted with 10 μl of $10^9$ CFU/mL). The evaluation criteria (○, Δ, x) shown in each table are the same as the criteria used in Verification Experiment 1. Table 3 also shows the results of performing the same verification experiment after storing the prepared staining liquids at 50° C. for 1 month.

TABLE 3

| Type of dye | Item number (manufacturer name) | Dye concentration of staining liquid | pH of staining liquid | Evaluation results immediately after preparation | After storage at 50° C. for 1 month |
|---|---|---|---|---|---|
| Ruthenium red | R2751 (Sigma-Aldrich) | 0.5% | 7.0 | ○ | X |
| Alcian blue | Alcian Blue 8GX (A9186, Sigma-Aldrich) | 0.5% | 4.0 | ○ | ○ |
|  |  | 0.3% | 4.0 | ○ | ○ |
|  |  | 0.2% | 4.2 | ○ | — |
|  |  | 0.1% | 4.4 | ○ | — |
|  |  | 0.05% | 4.6 | Δ | — |
|  | Alcian Blue 8GX (A5268, Sigma-Aldrich) | 0.3% | 3.1 | ○ | ○ |
|  | Alcian Blue 8GX (CDX-A0001-G250, Funakoshi Co., Ltd.) | 1.2% | 2.6 | ○ | — |
|  |  | 0.9% | 2.7 | ○ | — |
|  |  | 0.6% | 2.9 | ○ | — |
|  |  | 0.3% | 3.3 | ○ | — |

—: Non-implementation

| Type of dye | Item number | Dye concentration | Pseudomonas aeruginosa ATCC 15442 | Pseudomonas aeruginosa ATCC 27853 | Staphylococcus aureus ATCC 29213 |
|---|---|---|---|---|---|
| Ruthenium red | R2751 (Sigma-Aldrich) | 0.5% | ○ | ○ | ○ |
| Alcian Blue | Alcian Blue 8GX (A9186, Sigma-Aldrich) | 0.1% | ○ | ○ | ○ |
|  |  | 0.5% | ○ | ○ | ○ |
|  | Alcian Blue 8GX (CDX-A0001-G250, Funakoshi Co., Ltd.) | 0.3% | ○ | ○ | ○ |
|  |  | 1.2% | ○ | ○ | ○ |

As shown in Tables 3 and 4, it was confirmed that at least the ruthenium red aqueous solution with a concentration of 0.5% and the alcian blue aqueous solutions with a concentration of 0.05 to 1.2%, preferably 0.1 to 1.2%, could be effectively used as the staining liquids in the biofilm detection system of the present invention. Unlike ruthenium red, alcian blue was excellent in storage stability in the form of an aqueous solution. It was also confirmed that ruthenium red and alcian blue could be used stably as the staining liquids simply by dissolving them in water without adjusting the pH of the aqueous solutions.

Verification Experiment 3: Verification of Blotting Membrane

In Verification Experiment 3, the membrane sheets made of various materials shown in Table 5 were used as the blotting membrane used throughout steps 1 to 5, and the biofilm detection system (pretreatment: 30 seconds, staining treatment: 30 seconds, and decolorization treatment: 60 seconds; 2 minutes in total) was carried out to verify the practicality of the blotting membranes. Among the membranes shown in Table 5, PVDF (Amersham Hybond P)/hydrophilic treatment, PVDF (Immun-Blot)/hydrophilic treatment, and PVDF (Sequi-Blot)/hydrophilic treatment were prepared by subjecting, respectively, commercially available PVDF (Amersham Hybond P), PVDF (Immun-Blot), and PVDF (Sequi-Blot) to hydrophilic treatment. The hydrophilic treatment was carried out by immersing each commercially available membrane in 95 volume % ethanol for 10 minutes (hydrophilic treatment), followed by air drying (in actual use, a dry membrane is moistened with sterile water and then subjected to step 1). The pretreatment liquid used in step 2 (pretreatment step) and the decolorizing liquid used in step 4 (decolorization step) were a 5% polyoxyethylene lauryl ether (Blaunon El 1509, produced by Aoki Oil Industrial Co., Ltd.) aqueous solution. The staining liquid used in step 3 (staining step) was a 0.3% alcian blue (A9186, Sigma-Aldrich) aqueous solution (pH: 4.0).

After 1 minute of the decolorization treatment, the blotting membrane was taken out from the container, and the colored state was visually confirmed. The results are shown in Tables 5 and 6. Table 5 shows the results of using, as the biofilm suspension, *Pseudomonas aeruginosa* PAO1 strain suspension (blotted with 10 μl of $10^9$ CFU/mL). Table 6 shows the results of using, as the biofilm suspensions, *Pseudomonas aeruginosa* ATCC 15442, *Pseudomonas aeruginosa* ATCC 27853, and *Staphylococcus aureus* ATCC 29213 suspensions (blotted with 10 μl of $10^9$ CFU/mL). The evaluation criteria (○, Δ, x) shown in each table are the same as the criteria used in Verification Experiment 1.

TABLE 5

| Type of membrane | Product name | Pore size (μm) | Model number (manufacturer name) | Evaluation results |
|---|---|---|---|---|
| Nitrocellulose | Supported Nitrocellulose | 0.2 | 162-0097 (Bio-Rad) | ○ |
|  | Supported Nitrocellulose | 0.45 | 162-0094 (Bio-Rad) | ○ |
|  | Non-Supported Nitrocellulose | 0.2 | 162-0146 (Bio-Rad) | ○ |
|  | Supported Nitrocellulose | 0.2 | 1060019 (GE) | ○ |

TABLE 5-continued

| Type of membrane | Product name | Pore size (μm) | Model number (manufacturer name) | Evaluation results |
|---|---|---|---|---|
| | Supported Nitrocellulose | 0.45 | 1060020 (GE) | ○ |
| | Supported Nitrocellulose | 0.2 | 032-22663 (WAKO) | ○ |
| Cellulose | Cellulose mixed ester | 0.45 | A045H047A (ADVANTEC) | ○ |
| | Cellulose acetate | 0.2 | C020G047A (ADVANTEC) | ○ |
| Nylon | Non-charged nylon (Hybond-N)* | 0.45 | RPN2020N (GE) | ○ |
| | Positively-charged nylon (Hybond-N+) | 0.45 | RPN1510B (GE) | ○ |
| | Nylon (Nytran SPC (SuPerCharge)) | 0.45 | 10416230 (GE) | ○ |
| PVDF (hydrophilic polyvinylidene difluoride) | PVDF (Amersham Hybond P)/hydrophilic treatment | 0.42 | 10600100 (GE) | ○ |
| | PVDF (Immun-Blot)/hydrophilic treatment | 0.2 | 1620174 (GE) | ○ |
| | PVDF (Sequi-Blot)/hydrophilic treatment | 0.2 | 1620186 (GE) | ○ |
| | Hydrophilic PVDF | 0.45 | HVWP047S6 (Millipore) | ○ |
| Polytetrafluoroethylene (Teflon) | Hydrophilic PTFE (Omnipore) | 0.2 | JGWP04700 (Millipore) | ○ |
| | Hydrophilic PTFE (Omnipore) | 0.45 | JHWP04700 (Millipore) | ○ |

*Bipolar nylon membrane

TABLE 6

| Type of membrane | Pore size (μm) | Model number (manufacturer name) | Pseudomonas aeruginosa ATCC 15442 | Pseudomonas aeruginosa ATCC 27853 | Staphylococcus aureus ATCC 29213 |
|---|---|---|---|---|---|
| Nitrocellulose | | | | | |
| Supported Nitrocellulose | 0.2 | 162-0097 (Bio-Rad) | ○ | ○ | ○ |
| Supported Nitrocellulose | 0.45 | 162-0094 (Bio-Rad) | ○ | ○ | ○ |
| Supported Nitrocellulose | 0.2 | 1060019 (GE) | ○ | ○ | ○ |
| Supported Nitrocellulose | 0.2 | 032-22663 (WAKO) | ○ | ○ | ○ |
| Cellulose | | | | | |
| Cellulose acetate (filter membrane) | 0.2 | C020G047A (ADVANTEC) | ○ | ○ | ○ |
| Nylon | | | | | |
| Non-charged nylon | 0.45 | RPN2020N (GE) | ○ | ○ | ○ |
| Positively-charged nylon | 0.45 | RPN1510B (GE) | ○ | ○ | ○ |
| Nylon | 0.45 | 10416230 (GE) | ○ | ○ | ○ |
| PVDF/hydrophilic treatment | 0.45 | C020G047 (ADVANTEC) | ○ | ○ | ○ |
| Hydrophilic PTEE | 0.2 | JGWP04700 (Millipore) | ○ | ○ | ○ |

The results shown in Tables 5 and 6 revealed that although the blotting membranes could be used with or without charge in biofilm detection using wound blotting (biofilm detection system), polar materials or highly hydrophilic fibrous materials could be preferably used.

Experimental Example 2: Verification of Biofilm Detection System

The detection sensitivity of the biofilm detection method of the present invention was evaluated using the biofilm detection system established in Experimental Example 1 (Verification Experiments 1 to 3). Specifically, an aqueous solution containing hyaluronic acid and chondroitin sulfate, which were types of acidic mucopolysaccharides that were constituents of biofilm (aqueous solution containing 0.1 mg/mL sodium hyaluronate and 0.1 mg/mL sodium chondroitin sulfate) was used in place of the *Pseudomonas aeruginosa* biofilm suspension used in Experimental Example 1, and steps 2 to 4 (pretreatment in step 2: 30 seconds, staining treatment in step 3: 30 seconds, and decolorization treatment in step 4: 60 seconds; 2 minutes in total) were performed. The blotting membranes used in steps 2 to 4 were various membranes shown in Table 7 cut into a rectangle of 5 cm×5 cm. The pretreatment liquid used in step 2 (pretreatment step) and the decolorizing liquid used in step 4 (decolorization step) were a 5% polyoxyethylene lauryl ether (Blaunon EL 1509, produced by Aoki Oil Industrial Co., Ltd.) aqueous solution. The staining liquid used in step 3 (staining step) was the 0.3% alcian blue aqueous solution shown in Table 4.

After 1 minute of the decolorization treatment, the blotting membrane was taken out from the container, and the colored state was visually confirmed. The results are shown in Table 7. The evaluation criteria shown in Table 7 are the same as the criteria used in the above verification experiments.

TABLE 7

| Type of membrane | | Type of dye (manufacturer) | Results |
|---|---|---|---|
| Nylon | 0.45 µm non-charged nylon (Hybond-N): GE (RPN2020N) | Alcian Blue 8GX (A9186, Sigma-Aldrich) | ○ |
| | 0.45 µm positively-charged nylon (Hybond-N+): GE (RPN1510B) | | ○ |
| Nitrocellulose | 0.2 µm Supported Nitrocellulose (GE: 10600019) | | ○ |
| | 0.2 µm Supported Nitrocellulose (Bio-Rad: 162-0097) | | ○ |
| | | Alcian Blue 8GX (CDX-A0001-G250, Funakoshi Co., Ltd.) | ○ |

The above results confirmed that according to the biofilm detection method of the present invention, biofilm containing at least hyaluronic acid and chondroitin sulfate each at a concentration of 0.1 mg/mL could be visually detected.

Experimental Example 3: Verification of Biofilm Detection System

Using a model wound surface made from pig skin, the biofilm detection system established in Experimental Example 1 (Verification Experiments 1 to 3) was verified.
(1) Preparation of Model Wound Surface In the center of the surface of commercially available pig skin pieces (5 cm×5 cm) prepared by removing hair from skin obtained from pigs slaughtered for food, 200 µL of various bacterial solutions (*Pseudomonas aeruginosa* PAO1, *Pseudomonas aeruginosa* ATCC 27853, *Staphylococcus aureus* ATCC 29213, and a mixture of these three bacteria; $10^9$ CFU/mL) were added dropwise and spread in a circle (1.5 to 2 cm in diameter). Then, culture was carried out at 37° C. for 3 days to prepare model wound surfaces with biofilm.

A membrane (Supported Nitrocellulose: Bio-Rad, 0.2 µm) (5 cm×5 cm) moistened with sterile water was applied to the model wound surface (pig skin) prepared above for 10 seconds (step 1: blotting), and then the peeled membrane was subjected to steps 2 to 4, as in Experimental Example 1. The pretreatment liquid used in step 2 (pretreatment step) and the decolorizing liquid used in step 4 (decolorization step) were a 5% polyoxyethylene lauryl ether (Blaunon EL 1509, produced by Aoki Oil Industrial Co., Ltd.) aqueous solution. The staining liquid used in step 3 (staining step) was a 0.3% alcian blue aqueous solution.

FIG. 6 shows images showing the colored state of the blotting membranes after the decolorization treatment (immediately after decolorization and after drying). This experiment also confirmed that the presence of biofilm on the wound surface could be clearly visualized on the blotting membrane, as in Experimental Example 1, and that the state was stably maintained even after the blotting membrane dried. As in Experimental Example 1, it was confirmed that as the blotting membrane dried, the bluish color in the background of the membrane became pale (color fading), and the contrast with the colored portion where the biofilm components were adsorbed became clearer, thereby significantly visualizing the presence of biofilm on the blotting membrane.

Experimental Example 4: Verification of Biofilm Detection System

In Experimental Examples 4 (1) and (2), as the biofilm detection system, the steps (pretreatment step, staining step, and decolorization step) shown in FIGS. 2 and 3 were each performed at different treatment times to verify the reactivity of biofilm (Tables 8 and 9). In this experimental example, the blotting membrane used was a nitrocellulose membrane with a pore size of 0.2 µm (trade name: Supported Nitrocellulose Membrane, Bio-Rad #1620097) cut into a rectangle of 5 cm×5 cm. In step 1, as in Experimental Example 1 or 2, in place of the step of attaching the blotting membrane to the wound surface to adsorb biofilm components, a *Pseudomonas aeruginosa* PAO1 strain suspension ($10^9$ CFU/mL) or a hyaluronic acid-containing aqueous solution (0.1 mg/mL sodium hyaluronate-containing aqueous solution) as the biofilm suspension was dropped (10 µL) on the surface of the above blotting membrane previously moistened with sterile water, thereby allowing the biofilm components to be adsorbed on the blotting membrane. The pretreatment liquid used in step 2 (pretreatment step) and the decolorizing liquid used in step 4 (decolorization step) were a 5% polyoxyethylene lauryl ether (Blaunon EL 1509, produced by Aoki Oil Industrial Co., Ltd.) aqueous solution. The staining liquid used in step 3 (staining step) was a 0.3% alcian blue (A9186, Sigma-Aldrich) aqueous solution (pH: 4.0).

After the decolorization treatment in step 4, the colored state of each blotting membrane was visually confirmed. The results are shown in Tables 8 and 9. The evaluation criterion (○) shown in Tables 8 and 9 is the same as the criterion used in Verification Experiment 1.

TABLE 8

| Biofilm component | Pretreatment step (seconds) | Staining step (seconds) | Decolorization step (seconds) | Evaluation results |
|---|---|---|---|---|
| *Pseudomonas aeruginosa* PAO1 strain suspension | 2 | 30 | 60 | ○ |
| | 5 | 30 | 60 | ○ |
| | 10 | 10 | 30 | ○ |
| | 10 | 10 | 60 | ○ |
| | 15 | 15 | 30 | ○ |
| | 60 | 30 | 60 | ○ |
| | 180 | 30 | 60 | ○ |

TABLE 8-continued

| Biofilm component | Pretreatment step (seconds) | Staining step (seconds) | Decolorization step (seconds) | Evaluation results |
|---|---|---|---|---|
| | 30 | 10 | 60 | ○ |
| | 30 | 20 | 60 | ○ |
| | 30 | 60 | 60 | ○ |
| | 30 | 300 | 60 | ○ |
| | 30 | 30 | 10 | ○ |
| | 30 | 30 | 15 | ○ |
| | 30 | 30 | 30 | ○ |
| | 30 | 30 | 60 | ○ |
| | 30 | 30 | 180 | ○ |
| | 30 | 30 | 300 | ○ |
| | 30 | 30 | 600 | ○ |
| | 2 | 20 | 15 | ○ |
| | 2 | 30 | 15 | ○ |
| | 2 | 30 | 20 | ○ |
| | 2 | 30 | 30 | ○ |
| | 2 | 20 | 20 | ○ |
| Hyaluronic acid-containing aqueous solution | 2 | 30 | 15 | ○ |
| | 2 | 30 | 30 | ○ |
| | 2 | 20 | 20 | ○ |

TABLE 9

| Biofilm component | Pretreatment step (seconds) | Staining step (seconds) | Decolorization step (seconds) | Evaluation results |
|---|---|---|---|---|
| *Pseudomonas aeruginosa* PAO1 strain suspension | 5 | 10 | 30 | ○ |
| | 5 | 30 | 30 | ○ |
| | 10 | 10 | 30 | ○ |
| | 10 | 10 | 60 | ○ |
| | 10 | 20 | 60 | ○ |
| | 10 | 30 | 15 | ○ |
| | 10 | 30 | 30 | ○ |
| | 15 | 15 | 30 | ○ |
| | 30 | 30 | 60 | ○ |

The results shown in Tables 8 and 9 confirmed that in the biofilm detection method using wound blotting (biofilm detection system), the pretreatment step could be completed in a minimum of 2 seconds, the staining step in a minimum of 10 seconds, and the decolorization step in a minimum of 10 seconds; and that even when the pretreatment step was extended for at least 180 seconds, the staining step for at least 300 seconds, and the decolorization step for at least 600 seconds, there was no effect on the reaction results. The preferred treatment time for each step was, but not limited to, pretreatment step: 2 to 60 seconds, staining step: 10 to 60 seconds, and decolorization step: 10 to 60 seconds. Considering the use in clinical practice, it is preferable to select and set the treatment time for each step from the above range so that the total time of these steps is within 2 minutes.

REFERENCE SIGNS LIST

1. Pretreatment liquid
2. Staining liquid
3. Decolorizing liquid
4. Blotting membrane
5. Immersion container
6. Container that contains pretreatment liquid, staining liquid, or decolorizing liquid
7. Tweezers
8. Draining member
Waste liquid container

The invention claimed is:
1. A reagent kit for detecting the presence of biofilm in test tissue, the reagent kit comprising:
   (a) a pretreatment liquid comprising at least one surfactant other than an anionic surfactant selected from the group consisting of nonionic surfactants, amphoteric surfactants, and cationic surfactants,
   (b) a staining liquid comprising ruthenium red or alcian blue,
   (c) a decolorizing liquid comprising at least one surfactant other than an anionic surfactant selected from the group consisting of nonionic surfactants, amphoteric surfactants, and cationic surfactants, and
   (d) a membrane capable of adsorbing biofilm and/or components thereof present in the test tissue;
   wherein the pretreatment liquid (a), the staining liquid (b), and the decolorizing liquid (c) are each contained in separate containers, and
   wherein after the membrane is brought into contact with the test tissue and released from contact, the pretreatment liquid (a), the staining liquid (b), and the decolorizing liquid (c) are brought into contact with the contact surface of the membrane in this order;
   wherein the nonionic surfactant used in the pretreatment liquid (a) and/or the decolorizing liquid (c) is at least one selected from a polyoxyethylene lauryl ether, a polyoxyethylene sorbitan fatty acid ester, a polyoxyalkylene alkyl ether, an alkyl polyglucoside, a polyoxyethylene polyoxypropylene glycol, and a polyglycerol fatty acid ester;

wherein the amphoteric surfactant used in the pretreatment liquid (a) and/or the decolorizing liquid (c) is at least one selected from alkyl betaine surfactants and amine oxide surfactants;

wherein the cationic surfactant used in the pretreatment liquid (a) and/or the decolorizing liquid (c) is at least one selected from dialkyldimethyl ammonium chloride and quaternary ammonium salt surfactants having a $C_{8-18}$ alkyl group; and wherein the membrane (d) is made of at least one fibrous material selected from cellulose-based fibers and hydrophilic fluororesin-based fibers.

2. The reagent kit for detecting biofilm according to claim 1, wherein the pretreatment liquid (a) and the decolorizing liquid (c) are aqueous solutions having the same composition.

3. The reagent kit for detecting biofilm according to claim 1, wherein the surfactant used in the pretreatment liquid (a) and/or the decolorizing liquid (c) is the cationic surfactant selected from dialkyldimethyl ammonium chloride and benzalkonium chloride; the amphoteric surfactant selected from alkyldimethylaminoacetic acid betaine and alkyldimethylamine oxide; or the nonionic surfactant selected from a polyoxyethylene sorbitan fatty acid ester, a polyoxyalkylene alkyl ether, a polyoxyethylene lauryl ether, an alkyl polyglucoside, a polyoxyethylene polyoxypropylene glycol, and a polyglycerol fatty acid ester.

4. The reagent kit for detecting biofilm according claim 1, further comprising at least one auxiliary device selected from an immersion container, a draining member, a waste liquid container, a container with a drainer, tweezers, sterile distilled water, and a dryer.

5. The reagent kit for detecting biofilm according to claim 1, wherein the pretreatment liquid (a), the staining liquid (b), and the decolorizing liquid (c) are each contained in a separate container with a lid that can be opened and closed.

6. The reagent kit for detecting the presence of biofilm according to claim 1, further comprising an instruction manual.

7. A method for detecting the presence of biofilm in test tissue, comprising the following steps 1 to 4:
(1) step 1 of bringing a membrane capable of adsorbing biofilm and/or components thereof into contact with test tissue;
(2) step 2 of releasing the membrane from contact with the test tissue, and then treating at least the contact surface of the membrane with the test tissue with (a) a pretreatment liquid comprising at least one surfactant other than an anionic surfactant selected from the group consisting of nonionic surfactants, amphoteric surfactants, and cationic surfactants;
(3) step 3 of treating, with (b) a staining liquid comprising ruthenium red or alcian blue, at least the contact surface with the test tissue of the membrane treated with the pretreatment liquid (a); and
(4) step 4 of treating, with (c) a decolorizing liquid comprising at least one surfactant other than an anionic surfactant selected from the group consisting of nonionic surfactants, amphoteric surfactants, and cationic surfactants, at least the contact surface with the test tissue of the membrane treated with the staining liquid (b);
wherein
the nonionic surfactant used in the pretreatment liquid (a) and/or the decolorizing liquid (c) is at least one selected from a polyoxyethylene lauryl ether, a polyoxyethylene sorbitan fatty acid ester, a polyoxyalkylene alkyl ether, an alkyl polyglucoside, a polyoxyethylene polyoxypropylene glycol, and a polyglycerol fatty acid ester;

wherein the amphoteric surfactant used in the pretreatment liquid (a) and/or the decolorizing liquid (c) is at least one selected from alkyl betaine surfactants and amine oxide surfactants;

the cationic surfactant used in the pretreatment liquid (a) and/or the decolorizing liquid (c) is at least one selected from dialkyldimethyl ammonium chloride and quaternary ammonium salt surfactants having a $C_{8-18}$ alkyl group; and the membrane (d) is made of at least one fibrous material selected from cellulose-based fibers and hydrophilic fluororesin-based fibers.

8. The method for detecting the presence of biofilm according to claim 7, wherein the pretreatment liquid (a) and the decolorizing liquid (c) are aqueous solutions having the same composition.

9. The method for detecting the presence of biofilm according to claim 7, wherein the surfactant used in the pretreatment liquid (a) and/or the decolorizing liquid (c) is the cationic surfactant selected from dialkyldimethyl ammonium chloride and benzalkonium chloride; the amphoteric surfactant selected from alkyldimethylaminoacetic acid betaine and alkyldimethylamine oxide; or the nonionic surfactant selected from a polyoxyethylene sorbitan fatty acid ester, a polyoxyalkylene alkyl ether, a polyoxyethylene lauryl ether, an alkyl polyglucoside, a polyoxyethylene polyoxypropylene glycol, and a polyglycerol fatty acid ester.

10. The method for detecting the presence of biofilm according to claim 7, wherein the step 2 of (2) is performed for 2 to 60 seconds, the step 3 of (3) is performed for 5 to 60 seconds, and the step 4 of (4) is performed for 10 to 120 seconds.

11. The method for detecting the presence of biofilm according to claim 7, wherein the test tissue is raw tissue in a wound with signs of clinical infection, a refractory wound, or a chronic wound.

12. The method for detecting the presence of biofilm according claim 7, further comprising step 5 of determining whether biofilm is present in the test tissue.

13. The method for detecting the presence of biofilm according to claim 12, wherein step 5 is a step of determining that biofilm is present in the test tissue when the contact surface with the test tissue of the membrane treated with the decolorizing liquid has a dye-derived coloring that contrasts with the background color of the membrane.

14. The method for detecting the presence of biofilm according to claim 7, wherein steps 2 to 4 are performed in any of the following ways (i) to (iii):
(i) steps 2 to 4 are performed by sequentially replacing the pretreatment liquid, the staining liquid, and the decolorizing liquid in an immersion container containing the membrane obtained in step 1;
(ii) steps 2 to 4 are performed by sequentially taking the membrane obtained in step 1 in and out of immersion containers separately containing the pretreatment liquid, the staining liquid, and the decolorizing liquid; and
(iii) steps 2 to 4 are performed by placing the membrane obtained in step 1 on the drainer surface of a container with a drainer, and sequentially spraying or dropping the pretreatment liquid, the staining liquid, and the decolorizing liquid so as to spread over the entire surface of the membrane.

15. The reagent kit for detecting biofilm according to claim 1, wherein the membrane (d) is made of at least one fibrous material selected from nitrocellulose, cellulose mixed ester, cellulose acetate, hydrophilic polyvinylidene difluoride, and hydrophilic polytetrafluoroethylene.

\* \* \* \* \*